United States Patent
Trietsch et al.

(10) Patent No.: US 10,532,355 B2
(45) Date of Patent: Jan. 14, 2020

(54) MICROFLUIDIC PLATE

(71) Applicant: MIMETAS B.V., Leiden (NL)

(72) Inventors: Sebastiaan Johannes Trietsch, Leiden (NL); Paul Vulto, Leiden (NL)

(73) Assignee: Mimetas B.V., Leiden (NL)

(*) Notice: Subject to any disclaimer, the term of this patent is extended or adjusted under 35 U.S.C. 154(b) by 223 days.

(21) Appl. No.: 15/579,717

(22) PCT Filed: Jun. 5, 2015

(86) PCT No.: PCT/NL2015/050416
§ 371 (c)(1),
(2) Date: Dec. 5, 2017

(87) PCT Pub. No.: WO2016/195480
PCT Pub. Date: Dec. 8, 2016

(65) Prior Publication Data
US 2018/0169656 A1  Jun. 21, 2018

(51) Int. Cl.
*B01L 3/00* (2006.01)
*G01N 1/10* (2006.01)
*C12M 3/06* (2006.01)

(52) U.S. Cl.
CPC ... *B01L 3/502738* (2013.01); *B01L 3/502715* (2013.01); *C12M 23/16* (2013.01);
(Continued)

(58) Field of Classification Search
CPC ......... B01L 2200/025; B01L 2200/027; B01L 2200/0684; B01L 2200/12;
(Continued)

(56) References Cited

U.S. PATENT DOCUMENTS 4,761,381 A  8/1988  Blatt et al.
5,573,729 A  11/1996  Belgardt et al.
(Continued)

FOREIGN PATENT DOCUMENTS

JP  2014-174139 A  9/2014
WO  WO 02/072264 A1  9/2002
(Continued)

OTHER PUBLICATIONS

Moreno et al., "Differentiation of neuroepithelial stem cells into functional dopaminergic neurons in 3D microfluidic cell culture", Lab on a Chip, 2010, vol. 15, No. 11, 2419-2428.
(Continued)

*Primary Examiner* — Jennifer Wecker
(74) *Attorney, Agent, or Firm* — BakerHostetler

(57) ABSTRACT

Microfluidic plate comprising a plurality of microfluidic networks and inlets providing access to the microfluidic networks, wherein each microfluidic network comprises a capillary pressure barrier and extends through a first plane, each inlet is formed by an inlet chamber having a bottom surface, a support structure is provided above each inlet, which support structure defines an opening and comprises at least one support member positioned at the opening such that a circle can be defined in a second plane extending parallel to the first plane, which circle has the largest possible diameter while being completely located within the opening and in contact with the at least one support member, and the support structure is configured such that a first empty space is formed, which first empty space extends from the second plane towards the inlet chamber and has the form of a right circular cone or a truncated right circle cone, wherein the circle forms a base plane of the right circular cone or the truncated right circle cone.

19 Claims, 23 Drawing Sheets

(52) U.S. Cl.
CPC ... *B01L 2200/025* (2013.01); *B01L 2200/027* (2013.01); *B01L 2200/0684* (2013.01); *B01L 2300/069* (2013.01); *B01L 2300/0829* (2013.01); *B01L 2400/0406* (2013.01); *B01L 2400/0487* (2013.01); *B01L 2400/0688* (2013.01); *B01L 2400/088* (2013.01)

(58) Field of Classification Search
CPC ....... B01L 2300/069; B01L 2300/0829; B01L 2300/0858; B01L 2400/0406; B01L 2400/0487; B01L 2400/0688; B01L 2400/086; B01L 2400/088; B01L 3/502715; B01L 3/502738; C12M 23/16
See application file for complete search history.

(56) References Cited

U.S. PATENT DOCUMENTS

| | | | |
|---|---|---|---|
| 6,271,040 | B1 | 8/2001 | Buechler |
| D465,853 | S | 11/2002 | Petersen |
| 6,499,365 | B1 | 12/2002 | Baumgartner |
| 6,601,613 | B2 | 8/2003 | McNeely et al. |
| 6,637,463 | B1 | 10/2003 | Lei et al. |
| 6,778,917 | B1 | 8/2004 | Jansen |
| 7,585,468 | B2 | 9/2009 | Jaghuber |
| 7,673,532 | B2 | 3/2010 | Wilmer |
| 7,674,432 | B2 | 3/2010 | Wilmer |
| 7,731,908 | B2 | 6/2010 | Lenz |
| 8,114,361 | B2 | 2/2012 | Reichmuth |
| 8,133,453 | B2 | 3/2012 | Molitor |
| 8,297,134 | B2 | 10/2012 | Wilmer |
| 8,377,396 | B2 | 2/2013 | Meinicke et al. |
| 8,408,079 | B2 | 4/2013 | Reicmuth et al. |
| D706,946 | S | 6/2014 | Lohn |
| D709,623 | S | 7/2014 | Lohn |
| 2004/0037739 | A1* | 2/2004 | McNeely ............ B01F 5/10 422/417 |
| 2004/0241051 | A1 | 12/2004 | Wyzgol et al. |
| 2007/0202538 | A1 | 8/2007 | Glezer et al. |
| 2007/0280856 | A1 | 12/2007 | Ulmanella et al. |
| 2014/0099705 | A1 | 4/2014 | Hung et al. |
| 2014/0220606 | A1 | 8/2014 | Puntambekar et al. |
| 2014/0261757 | A1 | 9/2014 | Katsumoto |

FOREIGN PATENT DOCUMENTS

| | | |
|---|---|---|
| WO | WO 2006/074665 A2 | 7/2006 |
| WO | WO 2010/086179 A2 | 8/2010 |
| WO | WO 2012/120101 A1 | 9/2012 |
| WO | WO 2014/038943 A1 | 3/2014 |

OTHER PUBLICATIONS

Phurimsak et al., "Phaseguide assisted liquid lamination for magnetic particle-based assays", Lab on a Chip, 2014, vol. 14, No. 13, 2334-2343.
Trietsch et al., "Microfluidic titer plate for stratified 3D cell culture", Lab on a Chip, 2013, vol. 13, No. 18, 3548-3554.
Vulto et al., "A microfluidic approach for high efficiency extraction of low molecular weight RNA", Lab on a Chip, 2010, vol. 10, No. 5, 610-616.
Yildirim et al., "Phaseguides as tunable passive microvalves for liquid routing in complex microfluidic networks", Lab on a Chip, 2014, vol. 14, No. 17, 3334-3340.

* cited by examiner

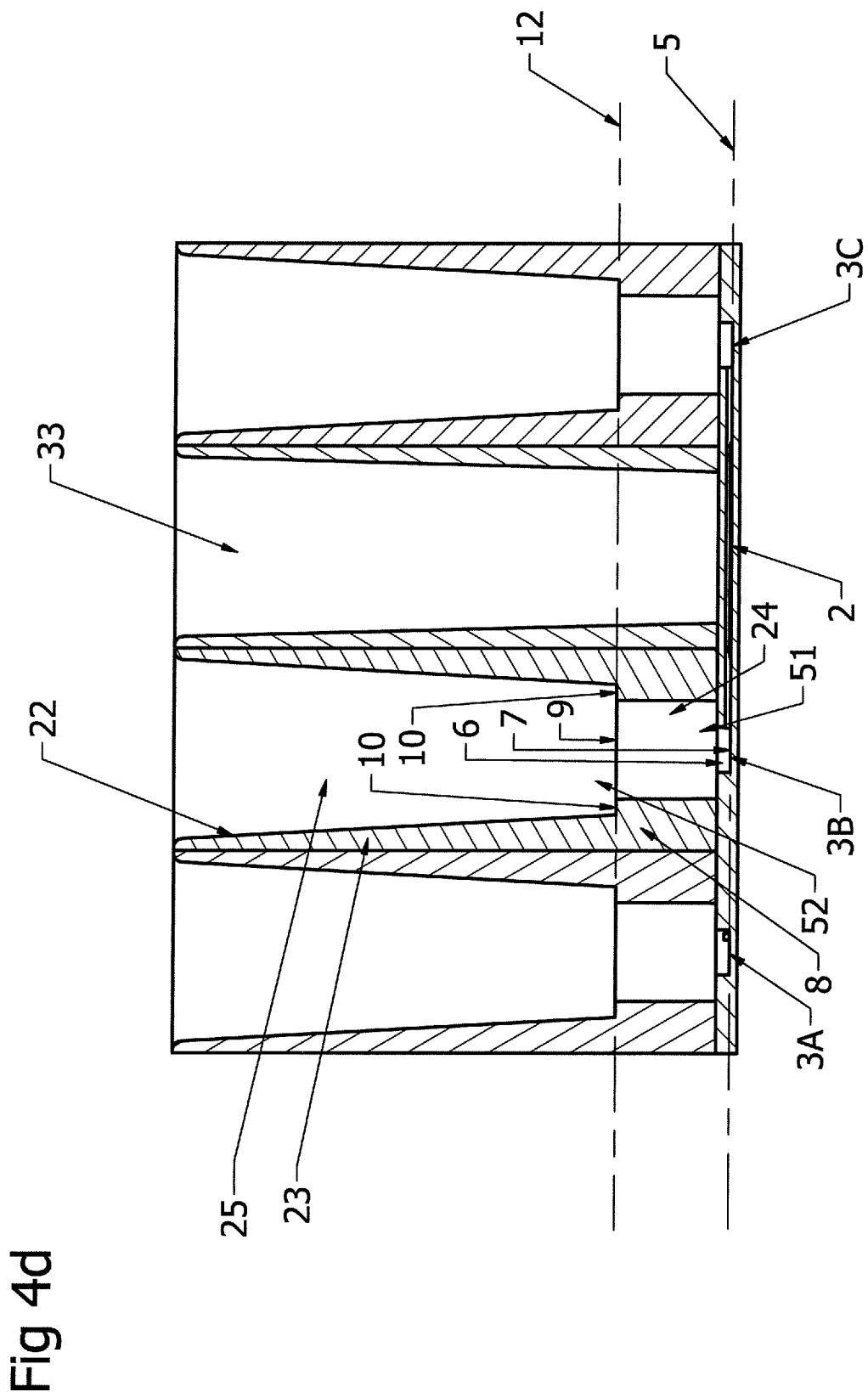

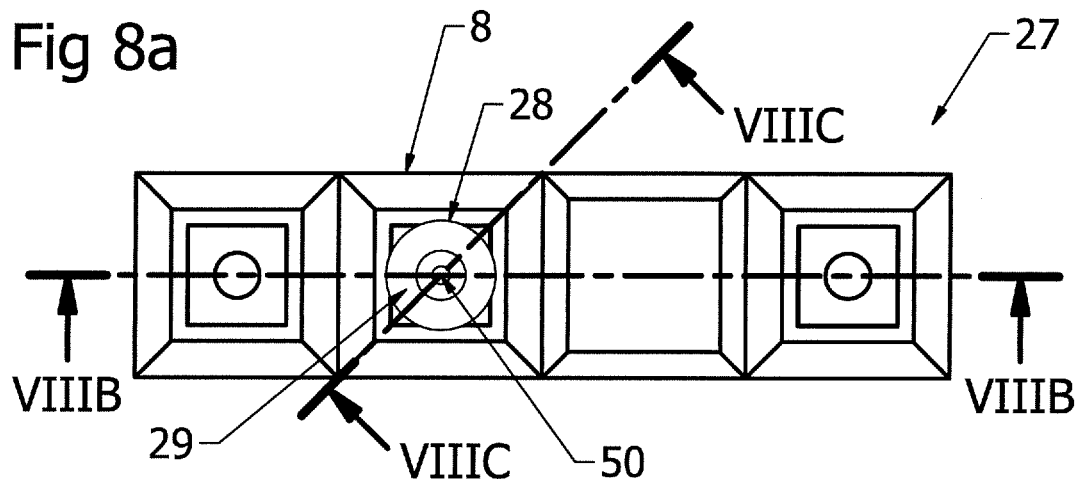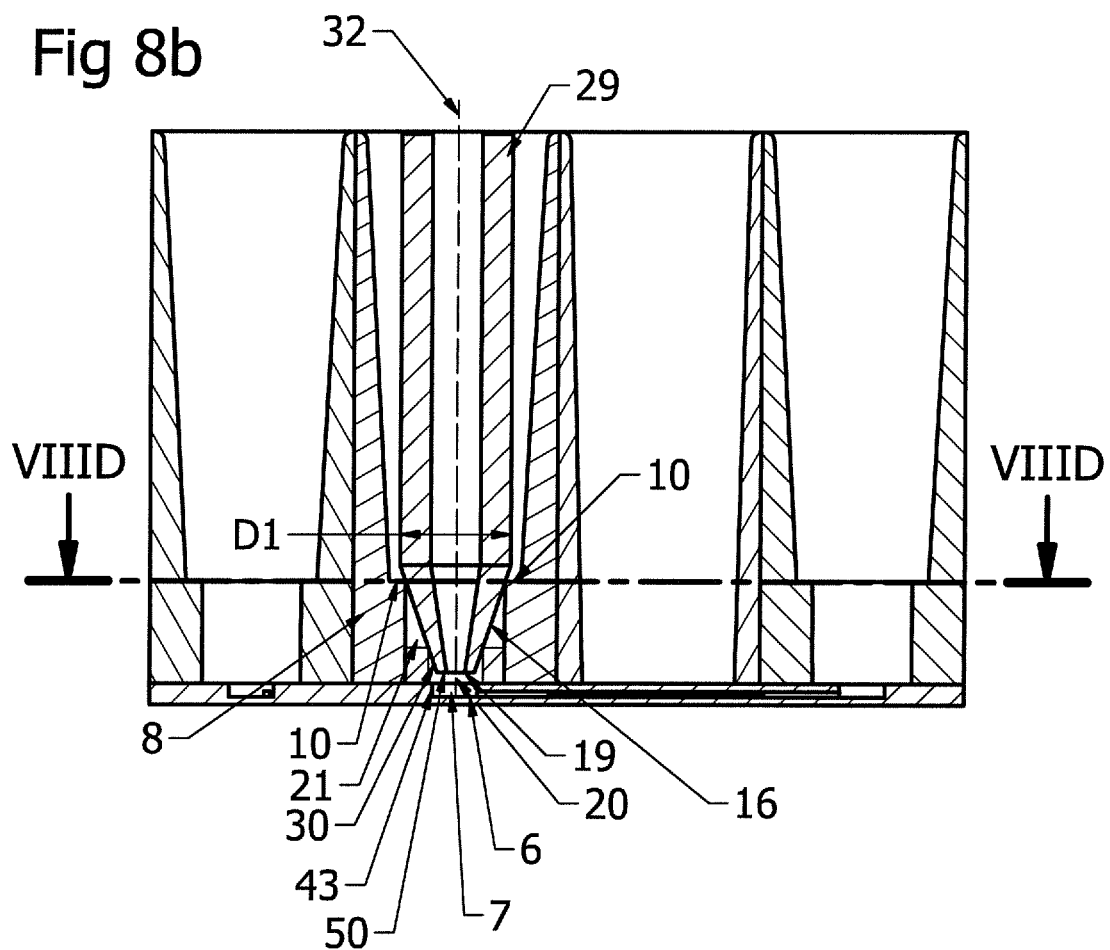

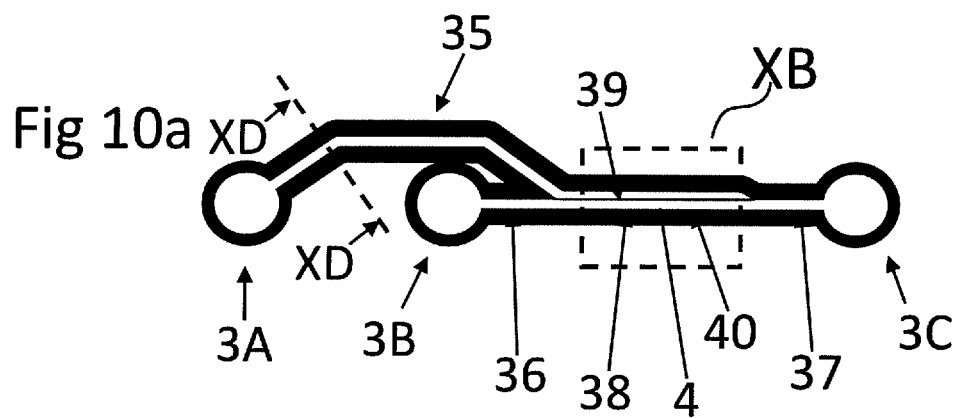
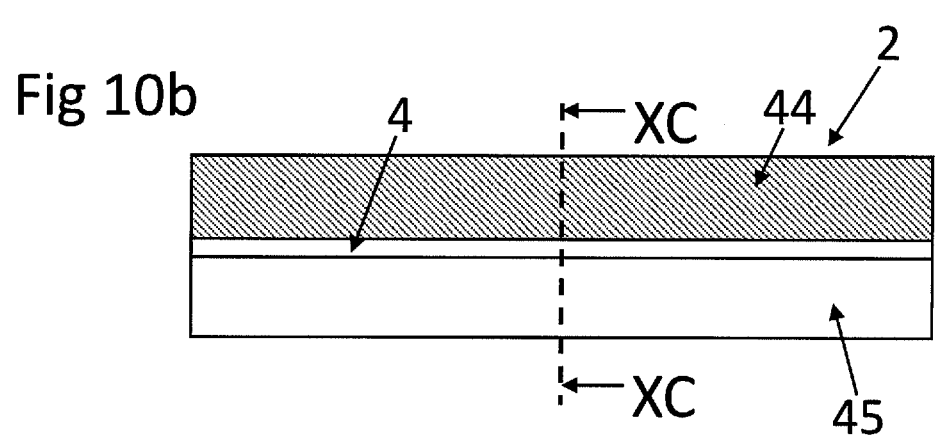

MICROFLUIDIC PLATE

FIELD OF THE INVENTION

The invention relates to a microfluidic plate comprising a plurality of microfluidic networks and inlets providing access to the microfluidic networks. Each microfluidic network comprises a capillary pressure barrier. Each inlet is formed by an inlet chamber having a bottom surface.

In practice, a fluid dispenser having a dispensing part with an end for dispensing fluid is used for inserting liquids and/or gels and/or gel precursors into the microfluidic network, thereby stopping or patterning at least one of the liquids/gels/gel precursors by means of a capillary pressure barrier. The microfluidic plate may be used for studying fluids or their contents or assessing the interaction between fluids or their contents. Examples of such usage may include assaying, reacting or culturing of life based particles such as cells, bacteria, yeast and others.

The capillary pressure barrier can for example divide a microfluidic chamber of the microfluidic network into a first chamber part and a second chamber part. A liquid, gel or gel precursor with life based particles such as cells may be discharged by the dispensing part of the fluid dispenser in the inlet. Said liquid or gel (precursor) will flow from the inlet into the first chamber part of the microfluidic chamber and is stopped, its advancement controlled or patterned due to the presence of a capillary pressure barrier. The liquid or gel (precursor) may be transported through the microfluidic network by capillary forces, by gravity or other actuating forces.

An example of the use of such a capillary pressure barrier is to selectively fill a microfluidic network with a first fluid, such as for instance a gel. The extend to which a microfluidic network is filled with said first fluid is determined by a capillary pressure barrier that halts advancement of the fluid in the network. Upon gelation the remainder of the microfluidic network may be filled with a second fluid such that exchange between the two fluids occurs or a reaction between the fluids or their components occurs. An example thereof shown ins the 3D culture of cells in an extracellular matrix gel that is flanked by a medium perfusion flow. This is extensively described in S. J. Trietsch, G. D. Israels, J. Joore, T. Hankemeier, P. Vulto, Microfluidic titer plate for stratified 3D cell culture, Lab Chip 2013, vol. 13, no. 18, pp. 3548-3554.

Other examples of use a capillary pressure barriers are given in C. Phurimsak, E. Yildirim, M. D. Tarn, S. J. Trietsch, T. Hankemeier, N. Pamme, P. Vulto, Phaseguide assisted liquid lamination for magnetic particle-based assays, Lab Chip, 2014, vol. 14, no. 13, pp. 2334-2343, P. Vulto, G. Dame, U. Maier, S. Makohliso, S. Podszun, P. Zahn, G. A. Urban, A microfluidic approach for high efficiency extraction of low molecular weight RNA, Lab Chip, 2010, vol. 10, no. 5, pp. 610-6, Edinson Lucumi Moreno, Siham Hachi, Kathrin Hemmer, Sebastiaan J. Trietsch, Aidos S. Baumuratov, Thomas Hankemeier, Paul Vulto, Jens C. Schwamborn and Ronan M. T. Fleming, Differentiation of neuroepithelial stem cells into functional dopaminergic neurons in 3D microfluidic cell culture, Lab Chip, Vol. 15, No. 11, pp. 2419-2428, US020070280856A1, US020040241051A1, US000004761381A, US000006271040B1, WO2006074665, U.S. Pat. No. 6,601,613B2, U.S. Pat. No. 6,637,463B1.

The capillary pressure barrier is responsible for stopping, controlling advancement or shaping the liquid-air meniscus. The pressure drop over a liquid air interface or meniscus is determined by its two principle radii of curvature as described by the Young-Laplace equation:

$$\Delta P = \gamma \left( \frac{1}{R_1} + \frac{1}{R_2} \right)$$

Where $\Delta P$ is the pressure drop over the meniscus, y the liquid-air surface tension and $R_1$ and $R_2$ the two principal radii of curvature of the meniscus.

A positive pressure drop over the meniscus is associated with a predominantly convex liquid meniscus shape. For a positive pressure drop an external pressure needs to be applied to advance the meniscus in downstream direction with respect to liquid filling. A negative pressure drop is associated with a predominantly concave meniscus shape. For a negative pressure drop no external pressure needs to be applied for the meniscus to advance in downstream direction with respect to the liquid filling. This is typically referred to as capillary filling or filling by capillary forces.

A capillary pressure barrier is a region in the microfluidic network that has different chemical properties or provides a change in geometry with respect to the surrounding microfluidic network, such that it increases the $\Delta P$ for a meniscus advancing on or beyond the capillary pressure barrier. Such capillary pressure barriers can be designed such that the pressure drop over an advancing meniscus changes from negative to positive at the barrier in a largely hydrauphilic network. Thus the filling of the hydrophilic parts of the microfluidic network is achievable by capillary forces only, while requiring an additional external pressure for the meniscus to advance on or past the capillary pressure barrier. A typical implementation of such a capillary pressure barrier is a region of lower hydrophilicity with respect to the hydrophilicity of the surrounding material. Examples are a hydrophobic patch, or stripe, or a less hydrophilic patch or stripe with respect to the ulterior network material. Alternatively, a change in geometry may also lead to a capillary pressure barrier, when designed such that the geometry forces a meniscus to change principal radii, such that the pressure drop over the meniscus increases. Examples of such geometrical capillary pressure barriers include an abrupt channel widening, pillars or posts in a chamber, a groove in the channel or chamber substrate as well as a protrusion of the material into the chamber volume. A combination between a difference in the wettability and geometry could also lead to a very effective capillary pressure barrier. Numerous types of capillary pressure barriers are described in WO2010086179, WO2012120101 and WO2014038943, which are all three incorporated herein by reference. Further information can be found in E. Yildirim, S. J. Trietsch, J. Joore, A. van den Berg, T. Hankemeier and P. Vulto, Phaseguides as tunable passive microvalves for liquid routing in complex microfluidic networks, Lab Chip 2014, vol. 14, no. 17, pp. 3334-3340 and U.S. Pat. No. 6,601,613.

The state of meniscus pinning is referred to when externally applied pressure is not sufficient to advance the liquid-air meniscus on or beyond the capillary pressure barrier. Advancement beyond the capillary pressure barrier is referred to as breaching the capillary pressure barrier. The burst pressure of the capillary pressure barrier is the pressure that needs to be applied externally for a liquid meniscus to breach the capillary pressure barrier.

Capillary pressure barriers are used for a range of applications including selectively patterning a liquid volume, a controlled advancement of the liquid-air meniscus, to stop a fluid flow, or as a differential valving concept in which the order of barrier breaching is controlled.

BACKGROUND OF THE INVENTION

The invention is based on the insight that in practise not all the microfluidic networks are filled in a satisfactory manner with the dispensed liquids, gels or gel precursors. When this is the case, the capillary pressure barrier may not act as required for the experiment. This means that there is a high risk that the experiment will not succeed.

SUMMARY OF THE INVENTION

The invention provides an improved or at least alternative microfluidic plate.

The microfluidic plate comprises a plurality of microfluidic networks and inlets providing access to the microfluidic networks, wherein;

each microfluidic network comprises a capillary pressure barrier and extends through a first plane, each inlet is formed by an inlet chamber having a bottom surface, a support structure is provided above each inlet, which support structure defines an opening and comprises at least one support member positioned at the opening such that a circle can be defined in a second plane extending parallel to the first plane, which circle has the largest possible diameter while being completely located within the opening and in contact with the at least one support member, and the support structure is configured such that a first empty space is formed, which first empty space extends from the second plane towards the inlet chamber and has the form of a right circular cone or a truncated right circle cone, wherein the circle forms a base plane of the right circular cone or the truncated right circle cone, the microfluidic plate comprises the following features A or B;

A) an apex of the right circular cone or an apical surface of the truncated right circle cone is located in the inlet chamber and on the bottom surface, or B) an apex of the right circular cone or an apical surface of the truncated right circle cone is located vertically above or in the inlet chamber and at a distance from the bottom surface, wherein an additional empty space is formed extending from the apex or the apical surface until the bottom surface, and a second empty space is formed, which second empty space extends from the second plane into the inlet chamber and is located outside the first empty space.

The fluid dispensers, such as a pipette, which are normally used to dispense fluid in the inlet of a microfluidic plate comprise a dispensing part with an end from which in use a fluid is dispensed, wherein the end has the form of a right circular cone or a truncated right circular cone and having a discharge opening from which the fluid can be discharged.

An advantage is reached when the microfluidic plate is used with a fluid dispenser wherein the end of the dispensing part fits within the first empty space of the support structure and is supported by the at least one support member when received in the opening, more specifically in the circle defined by the at least one support member.

In the situation that the end of the dispensing part has the form of a right circular cone, an apex thereof (having a discharge opening from which the fluid can be discharged) is located in or vertically above the inlet chamber and at a distance from the bottom surface when the end is received in the opening, more specifically in the circle defined by the at least one support member, and supported by the at least one support member. The fluid is discharged from the discharge opening in said apex.

In the situation that the end of the dispensing part has the form of a truncated right circular cone, the apical surface thereof (having a discharge opening from which the fluid can be discharged) is located in or vertically above the inlet chamber and at a distance from the bottom surface when the end is received in the opening, more specifically in the circle defined by the at least one support member, and supported by the at least one support member. The fluid is discharged from the discharge opening in said apical surface.

In the act of dispensing of the fluid in the inlets, the microfluidic plate is in general positioned on and supported by a horizontal surface, such that the microfluidic network extends (substantially) parallel to the horizontal surface. This can be seen as the horizontal use position of the microfluidic plate. Due to the support structure, the user is asserted that the end of the dispensing part of the fluid dispenser is located vertically above or in the inlet chamber and at a distance from the bottom surface of the inlet chamber when the end of the dispensing part is received in the opening of the support structure, more specifically in the circle defined by the at least one support member, and supported by the at least one support member. When a liquid, gel or gel precursors is dispensed with the end of the dispensing part in said position, the liquid will be dispensed into the inlet chamber. The microfluidic network is in fluid communication with the inlet chamber, which ensures that sufficient liquid will be transferred into the part of the microfluidic network dedicated to said liquid by for example the capillary pressure in the microfluidic network or gravity.

For the avoidance of doubt it is remarked that the use of the microfluidic plate according to the invention is by no means restricted to the horizontal use position. On the contrary the plate may be used under any angle. The horizontal use position is here merely mentioned as an example and a means to explain the invention.

In the known microfluidic plates, it may occur that the liquid was not dispensed precisely into the inlet chamber, but adjacent to that. In that case the pinning effects on the edge of an inlet or access hole may prevent fluid from entering the microfluidic channel network. In other examples, imprecise dispensing towards the corners of an inlet may result in that capillary forces maintained the droplet in the corner position, or wicking effects along the corners distributed the fluid to places other than the microfluidic network. In again other examples, imprecise dispensing adjacent to the inlet resulted in the fact that capillary pressure or gravity alone was not sufficient to fill the microfluidic network. Also, imprecise dispensing increases the risk that there is not enough fluid located in the inlet chamber to sufficiently fill the microfluidic network. In other known microfluidic plates it may occur that the end of the dispensing part (in practise also referred to as dispensing tip) makes a seal to the inlet bottom surface, thereby preventing gradual release of its content upon dispensing. This may result in the fact that the content is not released, or released under high pressure. This has the risk that liquid is actively propelled into the microfluidic network and the capillary pressure barrier is breached, resulting in malfunction of the microfluidic plate.

In yet another known microfluidic plate it may occur that the dispensing tip makes a seal to the support structure or inlet hole. In this case, the inlet chamber is vented through the microfluidic channel network. The pressure required for dispensing is in direct communication with the fluid that has been injected into the microfluidic device and may result in unrequired breaching of the capillary pressure barrier, resulting in malfunction of the microfluidic plate.

Active pressure is difficult to control, particularly when using a dispensing means such as a pipette that is designed to dispense accurate volume quantities rather than the pressure with which they are dispensed. For microfluidic plates comprising microfluidic networks having capillary pressure barriers this might pose a problem as too much applied pressure causes unwanted breaching of a capillary pressure barrier. For successfully filling a microfluidic device selectively with fluid it is thus required that in addition to positioning the dispensing means in the direct vicinity of a microfluidic channel inlet, a seal between the channel inlet and dispensing means is prevented, such that pressure build-up does not occur and the microfluidic system is primarily filled by capillary forces.

In the microfluidic plate according to the invention, the second empty space forms a vent to allow fluid communication between the inlet chamber and the surrounding environment when the end of the dispensing part is received in the opening and supported by the at least one support member.

The vent prevents or limits pressure build-up in the inlet chamber and the microfluidic network. A pressure increase may have a negative effect on the filling of the microfluidic network with the liquid. A pressure increase may for example push the liquid over the capillary pressure barrier. Thus the capillary pressure barrier is breached, potentially hampering the correct functioning of the microfluidic plate. An example of such a malfunctioning microfluidic plate is that upon unintential breaching of the capillary pressure barrier, a first liquid or gel is not selectively filling part of the network, but also fills part of the network with liquid that was intended to remain empty. Thus preventing the intended controlled interaction, assaying, reaction, or contacting of multiple liquids in the microfluidic plate.

In addition, providing a direct vent to the inlet chamber prevents that the microfluidic network itself acts as the conduit to release built up pressure. Thus the injection pressure of the dispensed liquid is effectively decoupled from the insertion of fluid into the microfluidic channel network. In an embodiment of the microfluidic plate, the opening has a non-circular form at the second plane.

In an embodiment of the microfluidic plate, the inlet provides access to a microfluidic channel of the microfluidic network and a vent area of the second plane extending between the support structure and the circle is larger than a channel area formed by a cross section perpendicular to the microfluidic channel.

This is an important feature of the invention, as the larger vent area implies a reduced hydraulic resistance with respect to the microfluidic channel network. A low hydraulic resistance means that the majority of glass or liquid outflux occurs through the vent area, rather than through the microfluidic channel network. This means that the dispensing pressure is effectively de-coupled from the velocity with which a fluid meniscus advances in the microfluidic channel network.

In an embodiment of the microfluidic plate, the support structure comprises inner walls which surround the opening and the at least one support member extends in a transverse direction from the inner walls. The at least one support member protrudes from the inner wall into the volume that is defined by the inner walls.

In an embodiment of the microfluidic plate, a guiding structure to in use guide an end of a dispensing part of a fluid dispenser towards the opening is provided on top of the support structure.

In an embodiment of the microfluidic plate, the at least one support member is located between the inlet chamber and the guiding structure.

In an embodiment of the microfluidic plate, the support structure is configured to form a reservoir to hold fluid, which reservoir is located above the inlet chamber.

In an embodiment of the microfluidic plate, the reservoir extends from the inlet chamber until the second plane.

In an embodiment of the microfluidic plate, the guiding structure is configured to form an additional reservoir to hold fluid, which additional reservoir is an extension of the reservoir.

In an embodiment of the microfluidic plate, the capillary pressure barrier is any one of:
  a hydrophobic patch, or stripe,
  a less hydrophilic patch or stripe with respect to the ulterior network material,
  a channel widening,
  one or more pillars or posts lined in a channel or chamber,
  a groove in the channel or chamber substrate,
  a protrusion of the material into the chamber volume.

In an embodiment of the microfluidic plate, the inlets provide access to a microfluidic channel of the microfluidic network and the capillary pressure barrier is present in the microfluidic channel or a microfluidic chamber connected to the microfluidic channel, and the capillary pressure barrier extends along the complete width or height of said microfluidic channel or microfluidic chamber.

For the avoidance of doubt, a person skilled in the art of biology, biochemistry or labware would recognise an embodiment of the microfluidic plate according to the invention as a microtiter plate that comprises a plurality of microfluidic networks and inlets providing access to the microfluidic networks, wherein;
  each microfluidic network comprises a capillary pressure barrier and extends through a first plane,
  each inlet is formed by an inlet chamber having a bottom surface,
  a well is provided that is positioned above each inlet; each well having an inner volume as defined by the circumference of the well, the well further comprising at least one protrusion into the inner volume, the protrusion being the support member
  the at least one protrusion defines an opening such that a circle can be defined in a second plane extending parallel to the first plane, which circle has the largest possible diameter while being completely located within the opening and in contact with the at least one protrusion, and a first empty space is formed, which first empty space extends from the second plane towards the inlet chamber and has the form of a right circular cone or a truncated right circle cone, wherein the circle forms a base plane of the right circular cone or the truncated right circle cone,
  the microfluidic plate comprises the following features A or B;
  A) an apex of the right circular cone or an apical surface of the truncated right circle cone is located in the inlet chamber and on the bottom surface, or
  B) an apex of the right circular cone or an apical surface of the truncated right circle cone is located vertically above or in the inlet chamber and at a distance from the bottom surface, wherein an additional empty space is formed extending from the apex or the apical surface until the bottom surface, and a second empty space is formed, which second empty space extends from the second plane into the inlet chamber and is located outside the first empty space.

The above described microfluidic plate is part of the invention and provides slightly modified wordings to explain an aspect of the invention In an embodiment of the microfluidic plate, the guiding structure and the reservoir structure are integrated as a single structure.

In an embodiment of the microfluidic plate, the support structures of the microfluidic plate are interconnected to form an integral structure.

In an embodiment of the microfluidic plate, the microfluidic plate coincides with at least parts of SBS microtiter plate dimensions.

In an embodiment of the microfluidic plate, the pitch between at least part of the first inlets coincides with the pitch between wells of a SBS microtiter plate.

In an embodiment of the microfluidic plate, the pitch between at least part of the first inlets is a multiple of 2.25 mm.

In an embodiment of the microfluidic plate, the second empty space has a cross section that corresponds with the second plane located outside the circle.

In an embodiment of the microfluidic plate, the additional empty space extends perpendicular to the second plane.

It will be clear to a person skilled in the art that any combination in any number of the features of the above defined embodiments of the microfluidic plate is possible.

The invention relates further to a kit of parts comprising a microfluidic plate according to the invention and a fluid dispenser, such as a pipette, having a dispensing part from which in use a fluid is dispensed, wherein the dispensing part comprises an end having the form of a right circular cone or a truncated right circular cone.

In an embodiment of the kit of parts, the end of the dispensing part fits within the first empty space of the support structure and the end of the dispensing part is supported by the at least one support member when received in the opening, more specifically in the circle defined by the at least one support member.

In an embodiment of the kit of parts;
the end of the dispensing part has the form of a right circular cone and an apex thereof is located in or vertically above the inlet chamber and at a distance from the bottom surface when the end is received in the opening, more specifically in the circle defined by the at least one support member, and supported by the at least one support member, or
the end of the dispensing part has the form of a truncated right circular cone and the apical surface is located in or vertically above the inlet chamber and at a distance from the bottom surface when the end is received in the opening, more specifically in the circle defined by the at least one support member, and supported by the at least one support member.

Seen in a cross sectional side view, the discharge opening at the apex of the right circular cone or at the apical surface of the truncated right circular cone of the end of the dispensing part is located between vertical lines extending through the outer edge of the inlet chamber, when the end of the dispensing part is received in the opening and supported by the at least one support member.

Seen from a top view, the discharge opening at the apex of the right circular cone or at the apical surface of the truncated right circular cone of the end of the dispensing part is located within the outer edge of the inlet chamber, when the end of the dispensing part is received in the opening and supported by the at least one support member.

In an embodiment of the kit of parts, the second empty space forms a vent to allow fluid communication between the inlet chamber and the surrounding environment when the end of the dispensing part is received in the opening, more specifically in the circle defined by the at least one support member, and supported by the at least one support member.

In an embodiment of the kit of parts, the openings of at least part of the support structures of the microfluidic plate are located at a predetermined distance from each other and the fluid dispenser comprises multiple dispensing parts having ends located at a corresponding predetermined distance from each other.

It will be clear that any combination of the features of any number of the above defined embodiments of the kit of parts is possible.

The invention relates further to a method of filling a microfluidic network, comprising the steps of:
providing a kit of parts according to the invention, and
placing the end of the dispensing part of the fluid dispenser in the opening of one of the support structures of the microfluidic plate such that the end is supported by the at least one support member to position the dispensing part vertically above or in the respective inlet chamber, and
discharging a liquid or gel or gel precursor in the inlet chamber via the dispensing part received in the opening and supported by the at least one support member.

In an embodiment said method further comprises the step of venting the inlet chamber and/or the second empty space through a vent area in the second plane extending between the support structure and the end of the dispensing part.

In an embodiment of the method;
the openings of at least part of the support structures of the microfluidic plate are located at a predetermined distance from each other and the fluid dispenser comprises multiple dispensing parts having ends located at a corresponding predetermined distance from each other,
the end of the discharge parts are placed in the openings of said at least part of the support structures such that the dispensing parts supported by the at least one support member to position the dispensing parts vertically above or in the respective inlet chambers, and
the liquid or gel or gel precursor is discharged in the inlet chambers via the dispensing parts received in the openings and supported by the at least one support member.

The invention further relates to a kit of parts comprising:
a fluid dispenser, such as a pipette, having a dispensing part with an end from which in use a fluid is dispensed, and
a microfluidic plate comprising a plurality of microfluidic networks and inlets providing access to the microfluidic networks, wherein;
each microfluidic network comprises a capillary pressure barrier,
each inlet is formed by an inlet chamber having a bottom surface,
a support structure is provided above each inlet, which support structure defines an opening to receive the end of the dispensing part and comprises at least one support member to support the end in order to block movement of the dispensing part received in the opening towards the bottom surface of the inlet beyond a predetermined distance from the bottom surface, the support structure is configured to position the end of the dispensing part received in the opening and supported by the at least one support member vertically above or in the inlet chamber, and the support structure comprises a vent allowing fluid communication between the inlet chamber and the surrounding environment when the end of the dispensing part is received in the opening and supported by the at least one support member.

The invention further relates to a microfluidic plate comprising a plurality of microfluidic networks and inlets providing access to the microfluidic networks, wherein;

each microfluidic network comprises a capillary pressure barrier, each inlet is formed by an inlet chamber having a bottom surface, a support structure is provided above each inlet, which support structure defines an opening to in use receive a dispensing part of a fluid dispenser, such as a pipette, and comprises at least one support member to in use support an end of the dispensing part in order to block movement of the dispensing part received in the opening towards the bottom surface of the inlet beyond a predetermined distance from the bottom surface, the support structure is configured to in use position the end of the dispensing part received in the opening and supported by the at least one support member vertically above or in the inlet chamber, and the support structure comprises a vent allowing fluid communication between the inlet chamber and the surrounding environment when in use the end of the dispensing part is received in the opening and supported by the at least one support member.

BRIEF DESCRIPTION OF THE DRAWINGS

Embodiments of the kit of parts, method and microfluidic plate according to the invention will be described by way of example only, with reference to the accompanying schematic drawings in which corresponding reference symbols indicate corresponding parts, and in which.

DETAILED DESCRIPTION OF THE DRAWINGS

Figure 1:
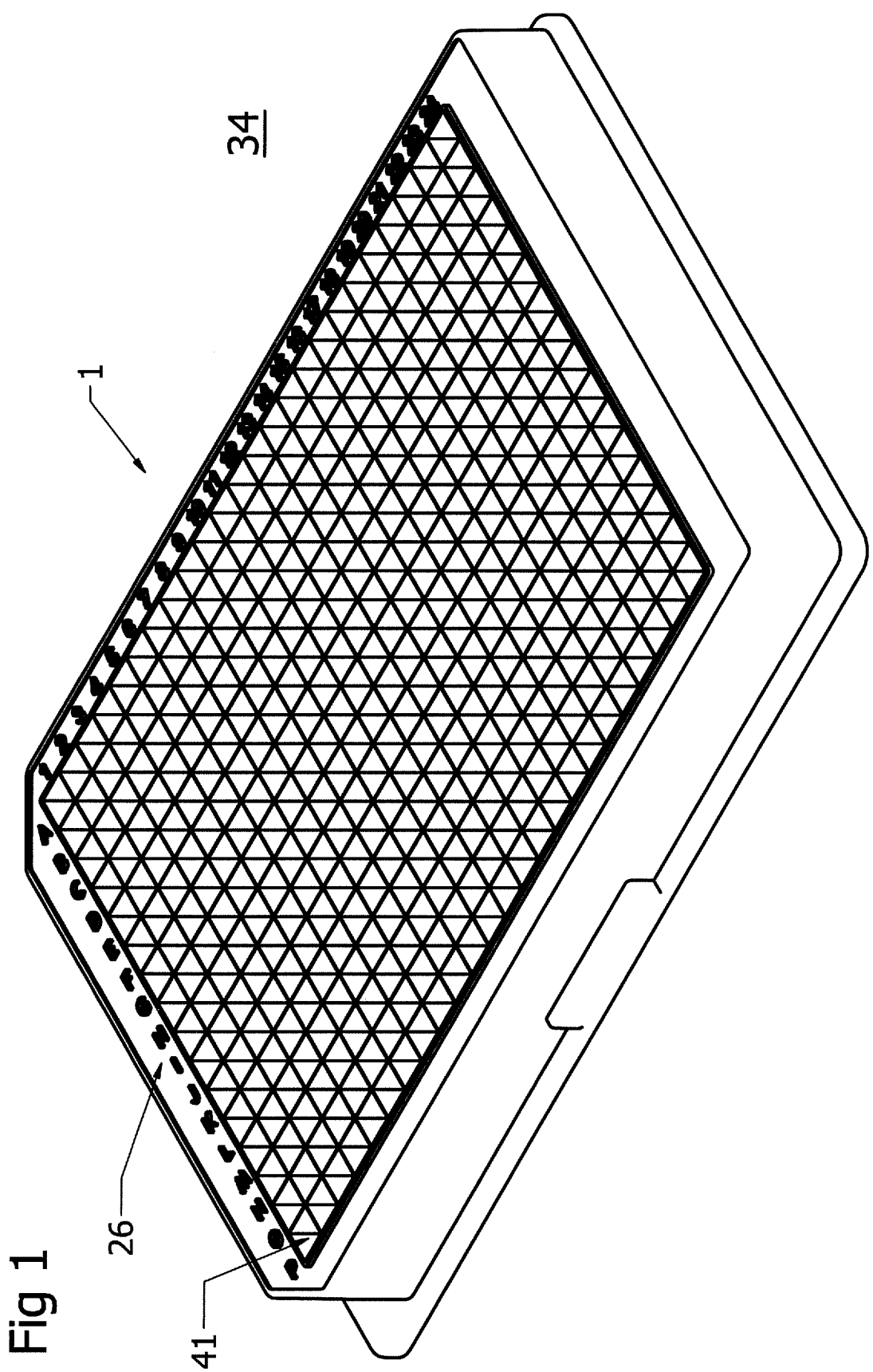
FIG. 1 schematically shows a view in perspective of a first embodiment of the microfluidic plate according to the invention, FIG. 2 schematically shows a top view of the microfluidic plate of FIG. 1, FIG. 3 schematically shows a bottom view of the microfluidic plate of FIG. 1, FIG. 4a schematically shows an enlarged top view of a part of the microfluidic plate of FIG. 1 dedicated to one of the microfluidic networks, FIG. 4b schematically shows a view in cross section along line IVB-IVB of FIG. 4a, FIG. 4c schematically shows a bottom view of microfluidic network of FIG. 4a, FIG. 4d schematically shows the view in cross section of FIG. 4b, wherein the first plane and second plane are indicated, FIG. 4e schematically shows the top view of FIG. 4a, wherein the circle defined by the support members is indicated, FIG. 4f schematically shows the view in cross section of FIG. 4b, wherein the first empty space in the form of a right circular cone is indicated, FIG. 4g schematically shows a view similar to FIG. 4f of a further embodiment of the microfluidic plate according to the invention, wherein the first empty space in the form of a right circular cone is indicated, FIG. 4h schematically shows a view similar to FIG. 4f of a further embodiment of the microfluidic plate according to the invention, wherein the first empty space in the form of a truncated right circular cone is indicated, FIG. 4i schematically shows a view similar to the FIG. 4f of a further embodiment of the microfluidic plate according to the invention, wherein the first empty space in the form of a truncated right circular cone is indicated, FIG. 5a schematically shows the top view of the FIG. 4a, wherein a dispensing part of a fluid dispenser is received in the opening of the support structure and supported by the support members, FIG. 5b schematically shows a view in cross section along line VB-VB of FIG. 5a, FIG. 5c schematically shows a view in cross section along line VC-VC of FIG. 5a, FIG. 5d schematically shows a view in cross section along line VD-VD of FIG. 5b, FIG. 5e schematically shows a view in perspective of the first embodiment of the kit of parts according to the invention of FIG. 5a, FIG. 6a schematically shows a top view of a second embodiment of the kit of parts according to the invention, FIG. 6b schematically shows a view in cross section along line VIB-VIB of FIG. 6a, FIG. 6c schematically shows a view in cross section along line VIC-VIC of FIG. 6a, FIG. 6d schematically shows a view in cross section along line VID-VID of FIG. 6b, FIG. 7a schematically shows a top view of a third embodiment of the kit of parts according to the invention, FIG. 7b schematically shows a view in cross section along line VIIB-VIIB of FIG. 7a, FIG. 7c schematically shows a view in cross section along line VIIC-VIIC of FIG. 7a, FIG. 7d schematically shows a view in cross section along line VIID-VIID of figure b, FIG. 8a schematically shows a top view of a fourth embodiment of the kit of parts according to the invention, FIG. 8b schematically shows a view in cross section along line VIIIB-VIIIB of FIG. 8a, FIG. 8c schematically shows a view in cross section along line VIIIC-VIIIC of FIG. 8a, FIG. 8d schematically shows a view in cross section along line VIIID-VIIID of FIG. 8b, FIG. 9a schematically shows a top view of a single support structure of FIG. 1, FIG. 9b schematically shows a top view of an alternative embodiment of the single support structure of FIG. 9a, FIG. 9c schematically shows a top view of another alternative embodiment of the single support structure of FIG. 9a, FIG. 10a schematically shows a top view of a single microfluidic network of FIG. 1, FIG. 10b schematically shows an enlarged view of the part XB of the microfluidic network of FIG. 10a, FIG. 10c schematically shows a view in cross section along line XC-XC of FIG. 10b, FIG. 10d schematically shows a view in cross section along line XD-XD of FIG. 10a, FIG. 11a schematically view similar to FIG. 10b of an alternative embodiment of the capillary pressure barrier, FIG. 11b schematically shows a view in cross section along line XB-XB of FIG. 11a, FIG. 11*c* schematically shows a view in cross section along line XC-XC of FIG. 11*a*, and the FIGS. 12*a-d* schematically show the operation of the kit of parts according to the invention in vertical cross section along the line VIIIB-VIIIB of FIG. 8*a*, and the FIGS. 12*e* schematically show the operation of the kit of parts according to the invention in vertical cross section along the line VIIIC-VIIIC of FIG. 8*a*.
Figure 2:
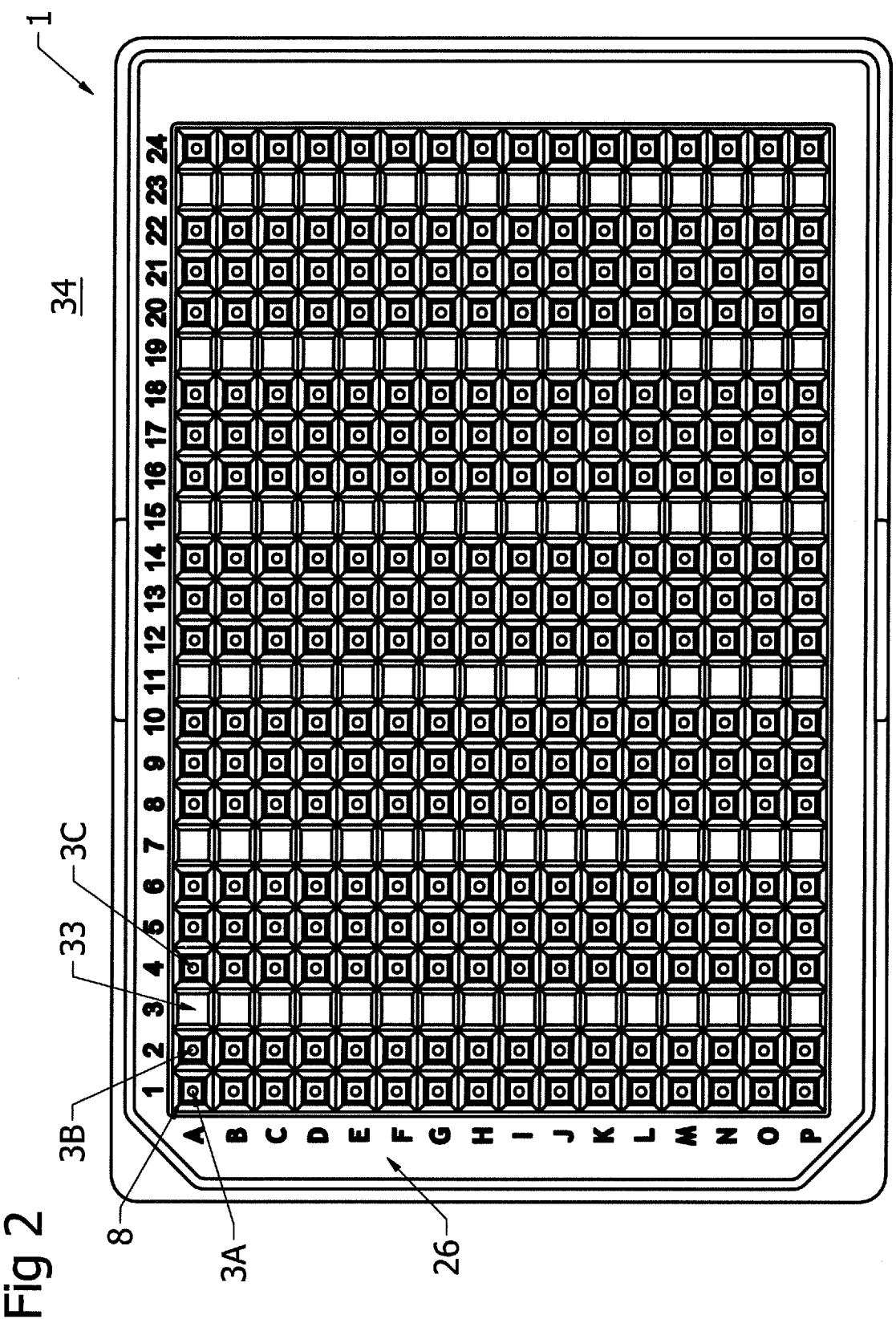
Figure 3:
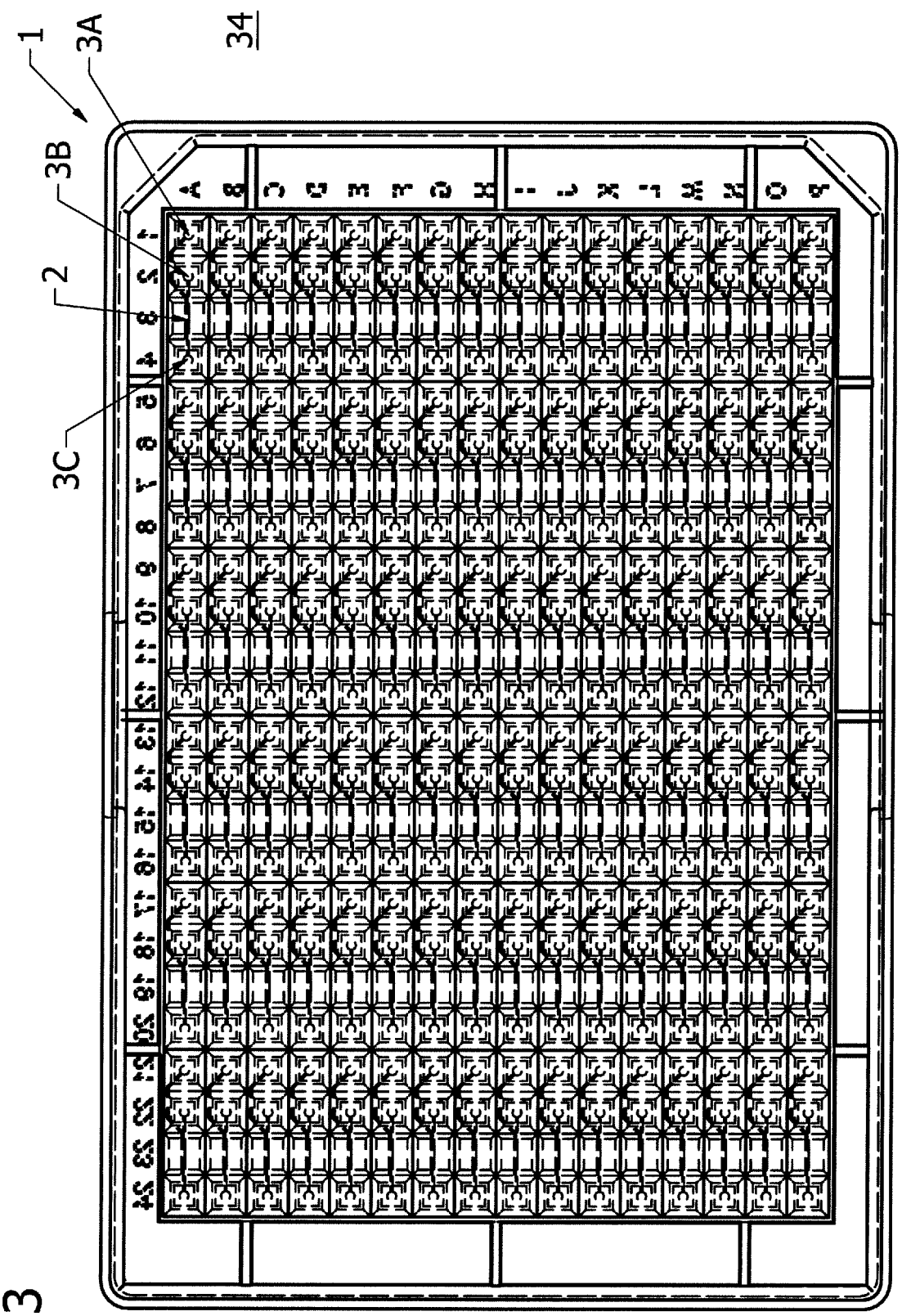

The FIGS. 1, 2 and 3 show a first embodiment of the microfluidic plate 1 according to the invention. The shown microfluidic plate 1 has the dimensions of a 384 well microtiter plate conform SBS standards and comprises 96 microfluidic networks 2. Each well 41 is connected to an inlet 3 of the microfluidic networks 2. Each microfluidic network 2 is in fluid communication with three inlets 3 (a first inlet 3A, a second inlet 3B, and a third inlet 3C). The pitch between the first inlets 3A located in one column corresponds to SBS microtiter plate dimensions, of in this case a 384 well plate. The same applies to the second inlets 3B and the third inlets 3C. A viewing window 33 is positioned above each microfluidic network 2. The viewing window 33 allows optical access to part of the microfluidic network 2. The microfluidic networks 2 are schematically indicated in the bottom view of FIG. 3.

The inlets 3A, 3B and 3C as well as the viewing window 33 are arranged as columns that all have the same function. The columns are spaced from one another with a pitch that corresponds to SBS microtiter plate dimensions, of in this case a 384 well plate. The pitch between wells of a 384 well plate corresponds to 4.5 mm. This is by example only, as the microfluidic plate according to the invention may have any pitch between wells of the same function or columns of wells of different function. For example a viewing window may be enlarged to yield a pitch of 9 mm.

The microfluidic plate according to the invention is by no means restricted to the arrangement of inlets and viewing windows as depicted in FIGS. 1, 2 and 3. On the contrary, microfluidic networks could be part of the invention that comprise any number of inlets and viewing windows.

The arrangement of inlets and viewing windows in columns of the same type is depicted here by means of example. The microfluidic plate according to the invention is by no means restricted to this arrangement.

When referring to an inlet, it is clear to a person skilled in the art of microfluidics, that an inlet could also be used as an outlet or vent.

Figure 4A:
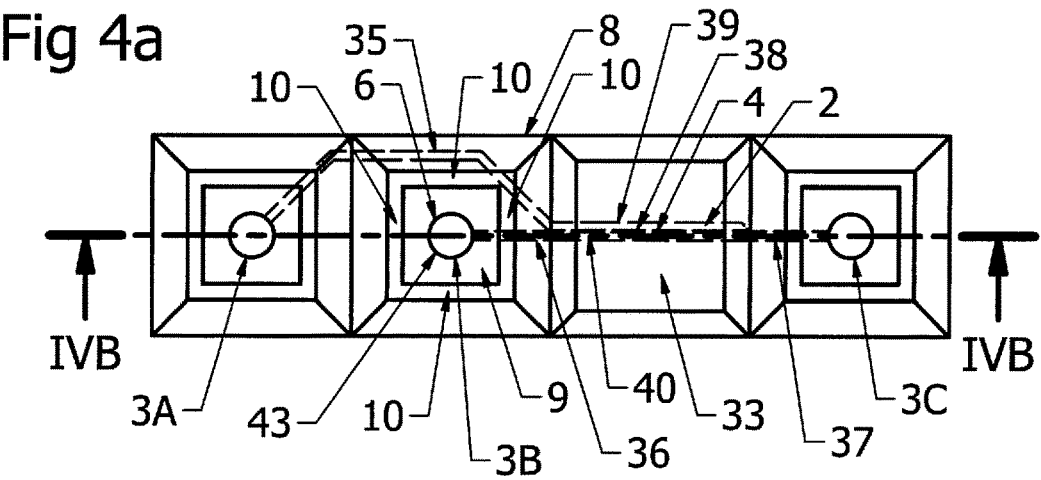
Figure 4B:
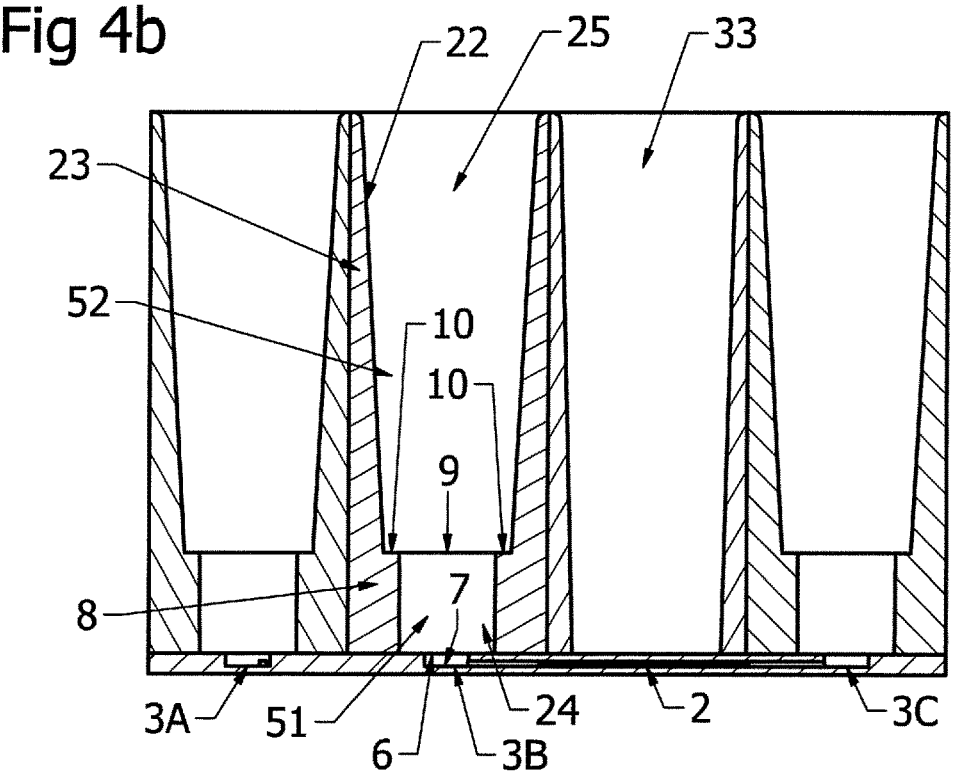
Figure 4C:
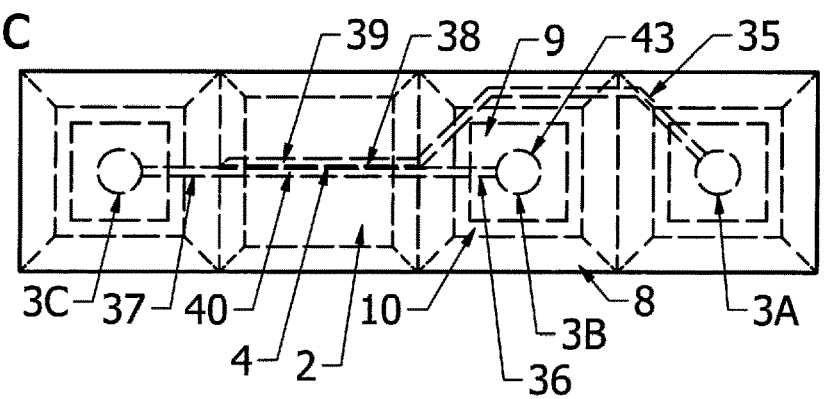

FIG. 4*a* shows an enlarged top view of a part of the microfluidic plate 1 of FIG. 1 dedicated to one of the microfluidic networks 2. The microfluidic network 2 comprises a first microfluidic channel 35 which is connected to the first inlet 3A and a second microfluidic channel 36 which is connected to the second inlet 3B and a third microfluidic channel 37 that is connected to the third inlet 3C. A capillary pressure barrier 4 is dividing the microfluidic chamber 38 into a first part 39 and a second part 40. The first microfluidic channel 35 is communicating with the first part 39 of the microfluidic chamber 38, while the second microfluidic channel 36 and the third channel 37 are communicating with the second part 40 of the microfluidic chamber 38. FIG. 4*b* shows a view in cross section along line IVB-IVB of FIG. 4*a*. FIG. 4*c* shows a bottom view of microfluidic network 2 of FIG. 4*a*.

The microfluidic plate 1 comprises a plurality of microfluidic networks 2 and inlets 3 providing access to the microfluidic networks 2. Each microfluidic network 2 comprises a capillary pressure barrier 4 and extends through a first plane 5 (see FIG. 4*d*). Each inlet 3 is formed by an inlet chamber 6 having a bottom surface 7. A support structure 8 is provided above each inlet 3, which support structure 8 defines an opening 9 and comprises at least one support member 10 positioned at the opening 9 such that a circle 11 (see FIG. 4*e*) can be defined in a second plane 12 (see FIG. 4*d*) extending parallel to the first plane 5, which circle 11 has the largest possible diameter while being completely located within the opening 9 and in contact with the at least one support member 10. The support structure 8 is configured such that a first empty space 14 is formed (see FIG. 4*f*), which first empty space 14 extends from the second plane 12 towards the inlet chamber 6 and has the form of a right circular cone 15 (or a truncated right circle cone 16 in an alternative embodiment). The circle 11 forms a base plane 17 of the right circular cone 15 (or the truncated right circle cone 16). An apex 18 of the right circular cone 15 (or an apical surface 19 of the truncated right circle cone 16) is located in the inlet chamber 6 and on the bottom surface 7. In an alternative embodiment the apex 18 of the right circular cone 15 (or an apical surface 19 of the truncated right circle cone 16) is located vertically above or in the inlet chamber 6 and at a distance from the bottom surface 7, wherein an additional empty space 20 is formed extending from the apex 18 (or the apical surface 19) until the bottom surface 7. A second empty space 21 (see FIGS. 4*e* and 4*f*) is formed, which second empty space 21 extends from the second plane 12 into the inlet chamber 6 and is located outside the first empty space 14.

Figure 4E:
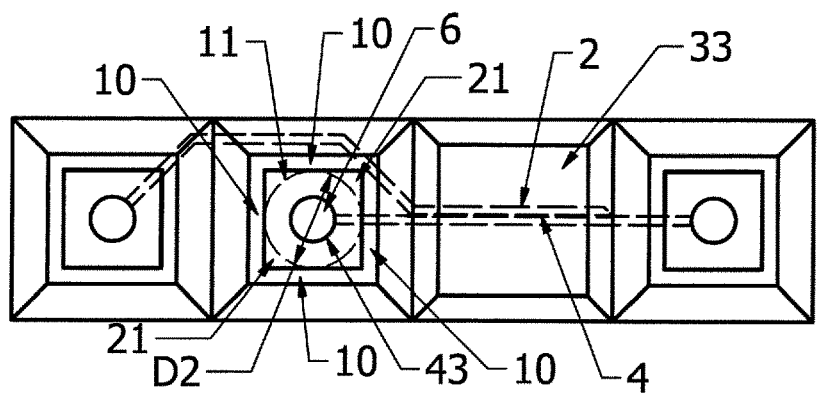
Figure 4F:
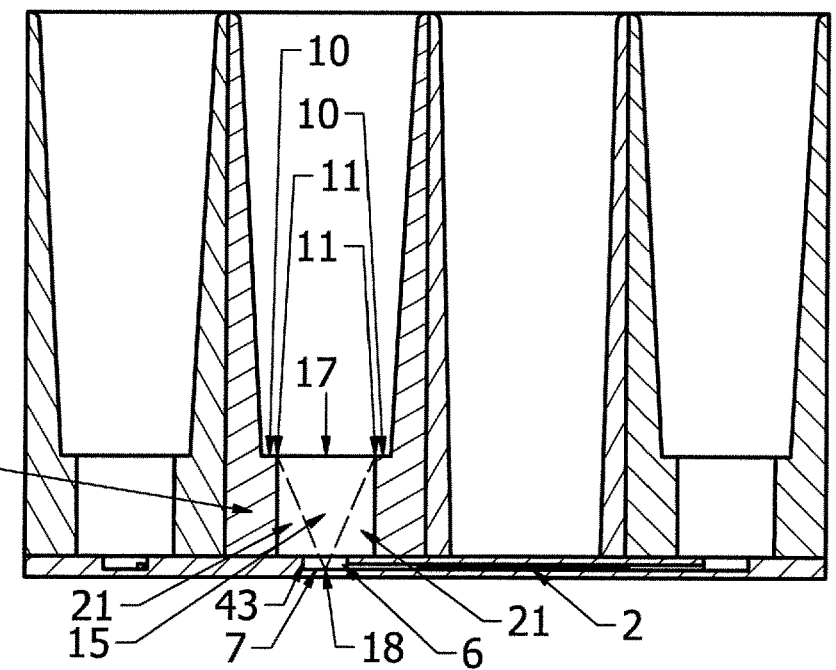

FIG. 4*d* shows a view in cross section of FIG. 4*b*, wherein the first plane 5 and second plane 12 are indicated. FIG. 4*e* shows the top view of FIG. 4*a*, wherein the circle 11 defined by the support members 10 is indicated. The support structure 8 comprises four support members 10. The support members 10 are connected to each other. FIG. 4*f* shows the view in cross section of FIG. 4*b*, wherein the first empty space 14 in the form of a right circular cone 15 is indicated. The apex 18 of the right circular cone 14 is located in the inlet chamber 6 and on the bottom surface 7. The second empty space 21 is shown in the FIGS. 4*e* and 4*f* and extends from the second plane 12 into the inlet chamber 6 and is located outside the first empty space 14. In use, the second empty space 21 functions as a vent 31.

The opening 9 shown in FIG. 4*e* has a non-circular form, more specifically the form of a square, at the second plane 12. The support structure 8 comprises inner walls 22 which surround the opening 9 and the at least one support member 10 extends in a transverse direction from the inner walls 22 (see FIG. 4*b*).

A guiding structure 23 to in use guide an end 30 of a dispensing part 23 of a fluid dispenser 28 towards the opening 9 is provided on top of the support structure 8. The at least one support member 10 is located between the inlet chamber 6 and the guiding structure 23.

The support structure 8 is configured to form a reservoir 24 to hold fluid, which reservoir 24 is located above the inlet chamber 6. The reservoir 24 has a first inner volume 51. The reservoir 24 extends from the inlet chamber 6 until the second plane 12. The guiding structure 23 is configured to form an additional reservoir 25 to hold fluid, which additional reservoir 25 is an extension of the reservoir 24 via the opening. The additional reservoir has a second inner volume 52. The first and second inner volumes 51, 52 of both reservoirs 24, 25 form the total inner volume of the combined reservoirs 24, 25. The at least one support member protrudes into said inner volume of the reservoirs 24, 25.

The support structures 8 of the microfluidic plate 1 are interconnected to form an integral structure 26. The microfluidic plate 1 has the dimensions of a microtiter plate, coinciding with SBS microtiter plate dimensions. The interconnected support structures 8 are positioned at a pitch similar to one or more wells 41 of the microtiter plate. The combined reservoirs 23 and 8 form one or more well 41. The pitch between the openings 9 of the interconnected support structures 8 coincide with SBS microtiter plate dimensions. It will be clear to the person skilled in the art that in a different embodiment, the microfluidic plate 1 is not limited to SBS standard dimensions but could have different dimensions for different purposes.

Figure 4G:
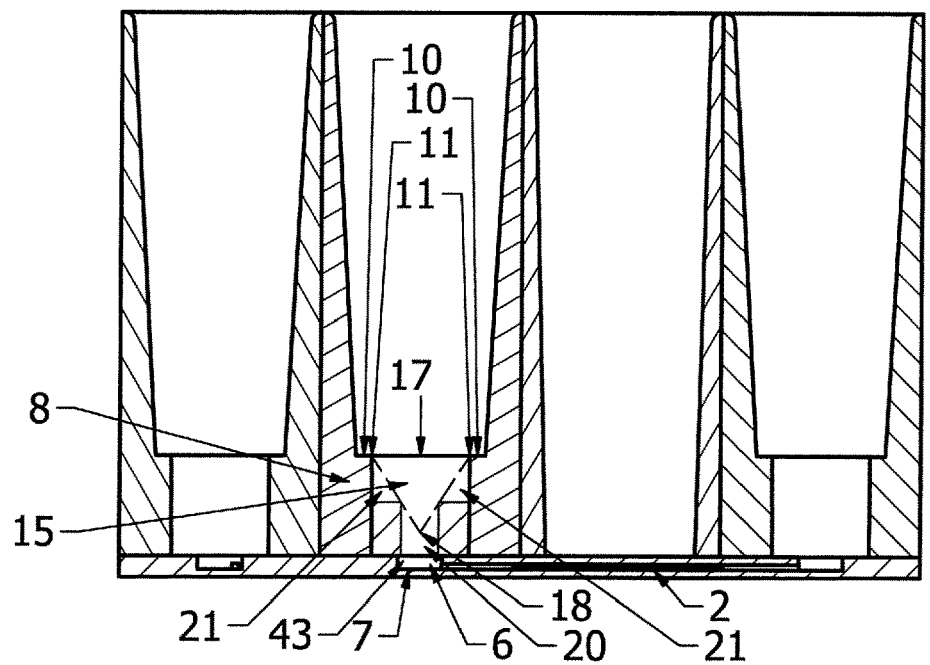

The FIG. 4g shows a view similar to the FIG. 4f of a further embodiment of the microfluidic plate 1 according to the invention, wherein the first empty space 14 in the form of a right circular cone 15 is indicated. The apex 18 of the right circular cone 15 is located vertically above and at a distance from the bottom surface 7. An additional empty space 20 is formed extending from the apex 18 until the bottom surface 7. A second empty space 21 is formed, which second empty space 21 extends from the second plane 12 into the inlet chamber 6 and is located outside the first empty space 14. In yet another embodiment, the apex 18 of the right circle cone 15 is located in the inlet chamber 6 and at a distance from the bottom surface 7.

Figure 4H:
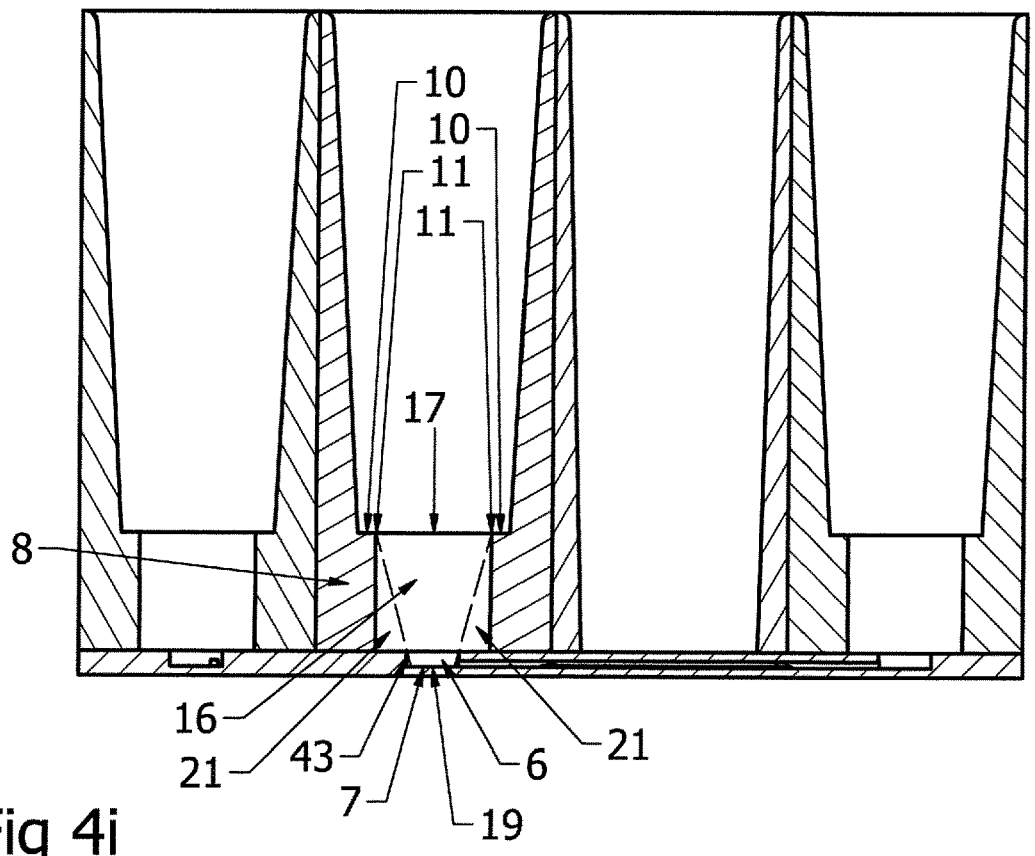

The FIG. 4h shows a view similar to FIG. 4f of a further embodiment of the microfluidic plate 1 according to the invention, wherein the first empty space 14 in the form of a truncated right circular cone 16 is indicated. The apical surface 19 of the truncated right circle cone 16 is located in the inlet chamber 6 and on the bottom surface 7. A second empty space 21 is formed, which second empty space 21 extends from the second plane 12 into the inlet chamber 6 and is located outside the first empty space 14.

Figure 4I:
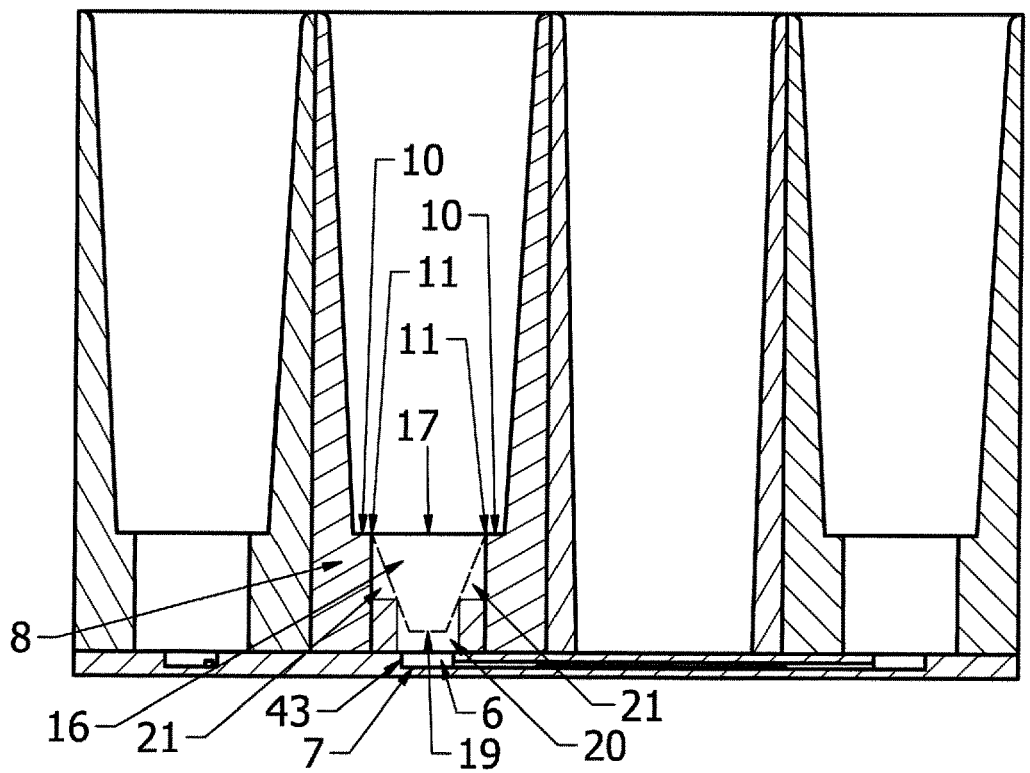

The FIG. 4i shows a view similar to that of FIG. 4f of a further embodiment of the microfluidic plate 1 according to the invention, wherein the first empty space 14 in the form of a truncated right circle cone 16 is indicated. The apical surface 19 of the truncated right circle cone 16 is located vertically above and at a distance from the bottom surface 7. An additional empty space 20 is formed extending from the apical surface 19 until the bottom surface 7. A second empty space 21 is formed, which second empty space 21 extends from the second plane 12 into the inlet chamber 6 and is located outside the first empty space 14. In yet another embodiment, the apical surface 19 of the truncated right circle cone 16 is located in the inlet chamber 6 and at a distance from the bottom surface 7.

In an embodiment, the microfluidic plate 1 comprises a plurality of microfluidic networks 2 and inlets 3 providing access to the microfluidic networks 2. Each microfluidic network 2 comprises a capillary pressure barrier 4. Each inlet 3 is formed by an inlet chamber 6 having a bottom surface 7. A support structure 8 is provided above each inlet 3, which support structure 8 defines an opening 9 to in use receive a dispensing part 29 of a fluid dispenser 28, such as a pipette. The support structure 8 comprises at least one support member 10 to in use support an end 30 of the dispensing part 29 in order to block movement of the dispensing part 29 received in the opening 9 towards the bottom surface 7 of the inlet 3 beyond a predetermined distance from the bottom surface 7. The support structure 8 is configured to in use position the end 30 of the dispensing part 29 received in the opening 9 and supported by the at least one support member 10 vertically above or in the inlet chamber 6. The support structure 8 comprises a vent 31 allowing fluid communication between the inlet chamber 6 and the surrounding environment 34 when in use the end of the dispensing part 29 is received in the opening 9 and supported by the at least one support member 10.

The fluid dispenser 28 may be a pipette. The pipette can be either with or without disposable tip. Pipettes come in a plurality of embodiments and comprise repeating pipettes, and single channel and multichannel pipettes. A plurality of shapes exists for the pipette tips of the pipette. The vast majority has a conical shape or truncated conical shape of the pipette tip or a conically shaped or truncated conically shaped apex of the pipette tip. It is clear for the skilled person that the pipette tip has a discharge opening 50 (from which the fluid is discharged) at the location of the apex 18 of the conical shape 15 or the apical surface 19 of the truncated cone shape 16. Also robotic dispensers may be used that come in a variety of shapes including multichannel heads. A commonly used embodiment of a single channel pipette is the Eppendorf Research® plus 0.5-10 µL pipette (Eppendorf AG, Germany, catalogue number 3120 000.020) as described in U.S. Pat. Nos. 7,674,432, 8,133, 453 and 8,297,134. A commonly used embodiment of a multichannel pipette is the 0.5-100 µL 8-channel Eppendorf Research® plus multichannel as described in U.S. Pat. No. 7,673,532 (Eppendorf AG, Germany, catalogue number 3122 000.019). A commonly used embodiment if a repeating pipette is the Eppendorf Multipette® M4 (Eppendorf AG, Germany, catalogue number 4982 000.012) as described in U.S. Pat. Nos. 8,114,361, 8,408,079, 5,573,729, 6,499,365, 6,778,917, 7,585,468 and 7,731,908.

A commonly used embodiment of a pipette tip is the Eppendorf 10 µL epT.I.P.S.® Standard (Eppendorf AG, Germany, catalogue number 0030 000.811) as described in U.S. Pat. No. D0,465,853. A commonly used embodiment of a pipette tip for use with repeating pipettes is the 0.1 mL Eppendorf Combitips Advanced® (Eppendorf AG, Germany, catalogue number 0030 089.405) as described in U.S. Pat. No. D0,709,623 and U.S. Pat. No. D0,706,946.

A commonly used embodiment of a pipetting robot is the Eppendorf epMotion® 50751 (Eppendorf AG, Germany, catalogue number 5075 000.301) as described in U.S. Pat. No. 8,377,396

A microfluidic network 2 comprises in general a channel, chamber, multiple channels or chambers or a combination thereof, wherein at least one dimension of at least one channel or chamber is less than one millimetre. A microfluidic network is typically constructed as a horizontally layered setup comprising a bottom substrate, a layer comprising the microfluidic network and a top substrate. The microfluidic layer may also be patterned into or onto either or both of the top and bottom substrates.

A capillary pressure barrier 4 is a region of decreased wettability or a widening in geometry in the channel or chamber geometry or material that requires a higher applied external pressure for a liquid-air meniscus to advance on or beyond the capillary pressure barrier. Capillary pressure barriers may be a hydrophobic patch, or stripe, or a less hydrophilic patch or stripe with respect to the ulterior chamber material as well as an abrupt channel widening, pillars or posts in a chamber, a groove in the channel or chamber substrate as well as a protrusion of the material into the chamber volume. Also a combination of the aforementioned may result in a capillary pressure barrier. An inlet 3 has an inlet chamber 6 which is in fluid communication with part of the microfluidic channel network 2. A typical inlet chamber is provided as a hole in the top-substrate of the microfluidic device. The inlet chamber (or hole) provides a space in which a liquid or gel or gel precursor can be deposited and which is further transported into the microfluidic network by capillary forces, meniscus forces, by gravity or by active pressure. The inlet chamber may, but does not necessarily need to be constructed out of the same material as the support structure.

A vent 31 is a connection with the surrounding atmosphere 34 that prevents or limits pressure build-up upon injecting a fluid in a volume. In the case that the pipette tip seals the inlet chamber, any pressure build-up can only be released by displacement of fluid in the microfluidic network. In this case, precise control is required over the injection pressure in order to prevent unrequired breaching of the capillary pressure barrier. The second empty space 21 according to the invention assures direct communication between the inlet 3 and the surrounding atmosphere 34 other than through the microfluidic network 2. The second empty space 21 thus acts as a vent 31 for the release of fluid from the fluid dispenser 28 in the inlet 3. The injection pressure of the dispensed fluid can effectively be decoupled from the insertion of fluid into the microfluidic channel network.

Figure 5A:
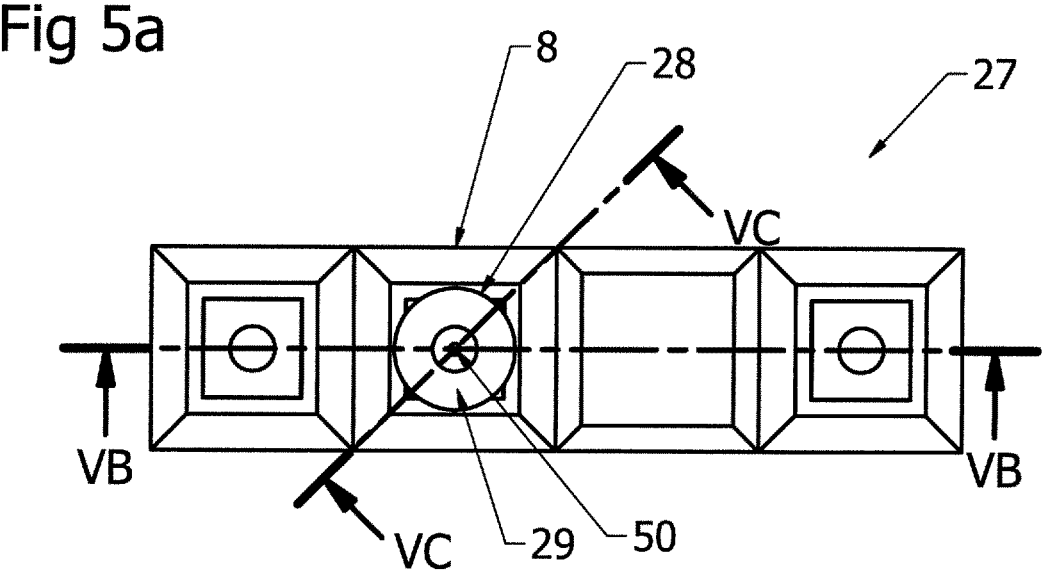
Figure 5B:
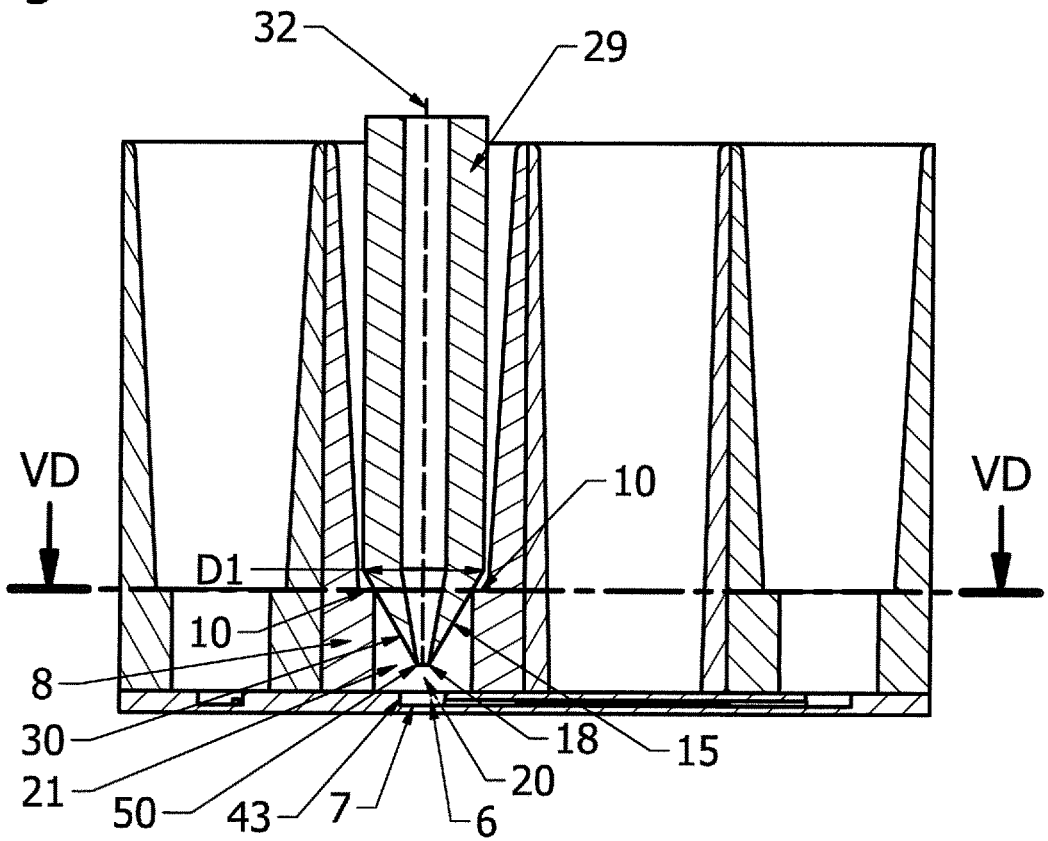
Figure 5C:
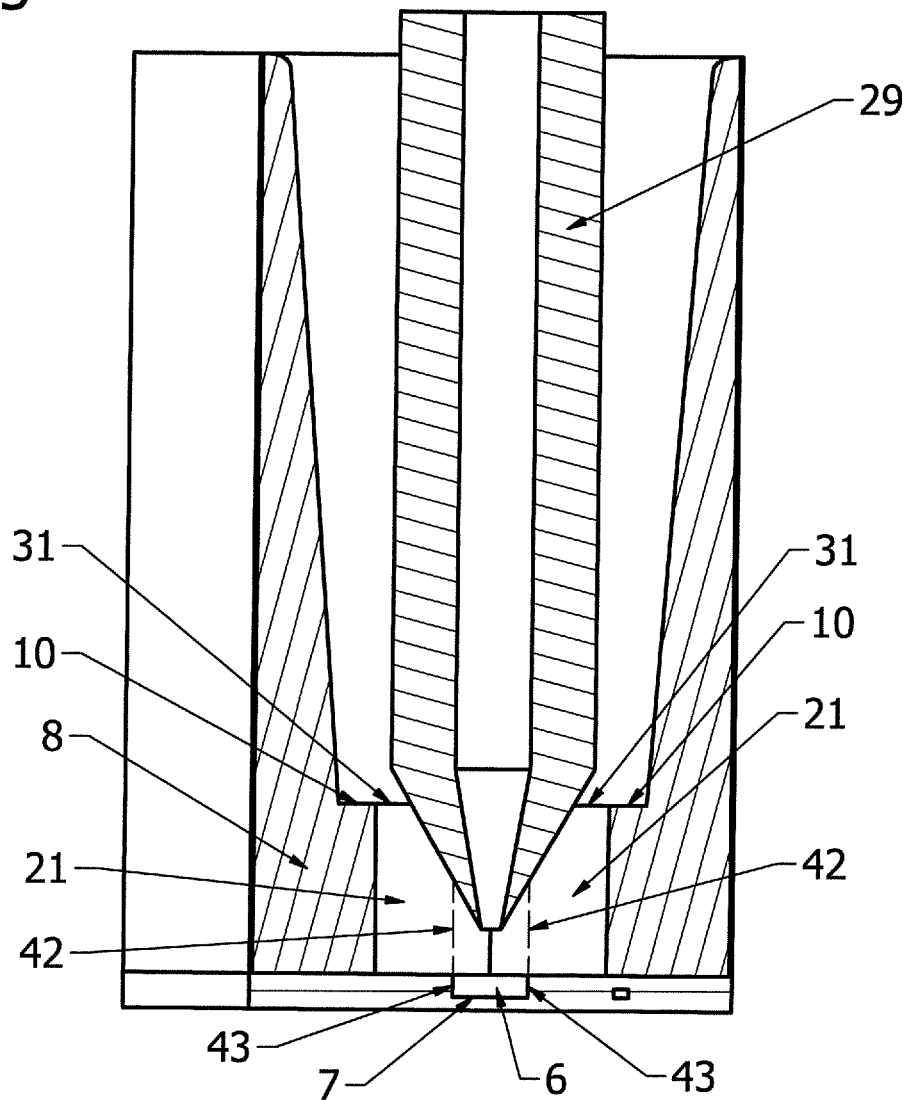
Figure 5D:
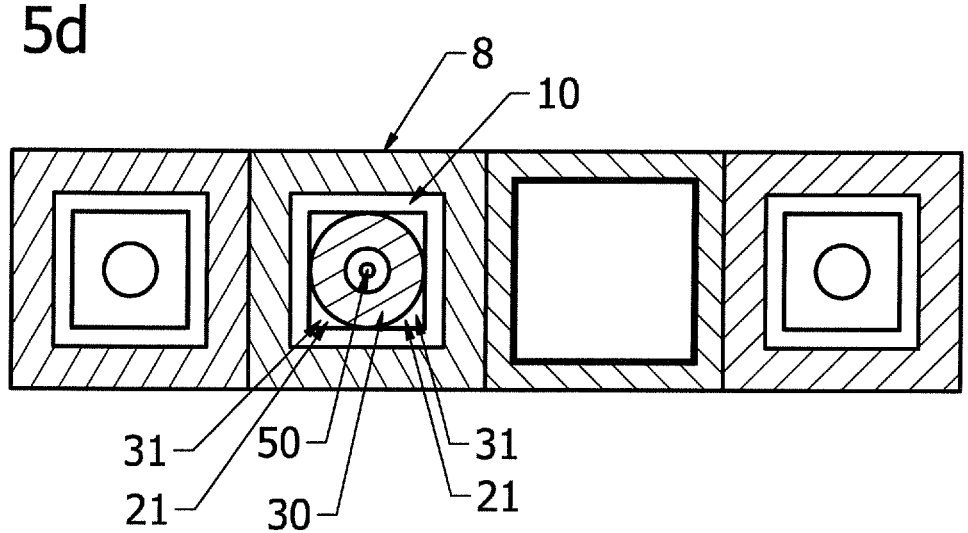
Figure 5E:
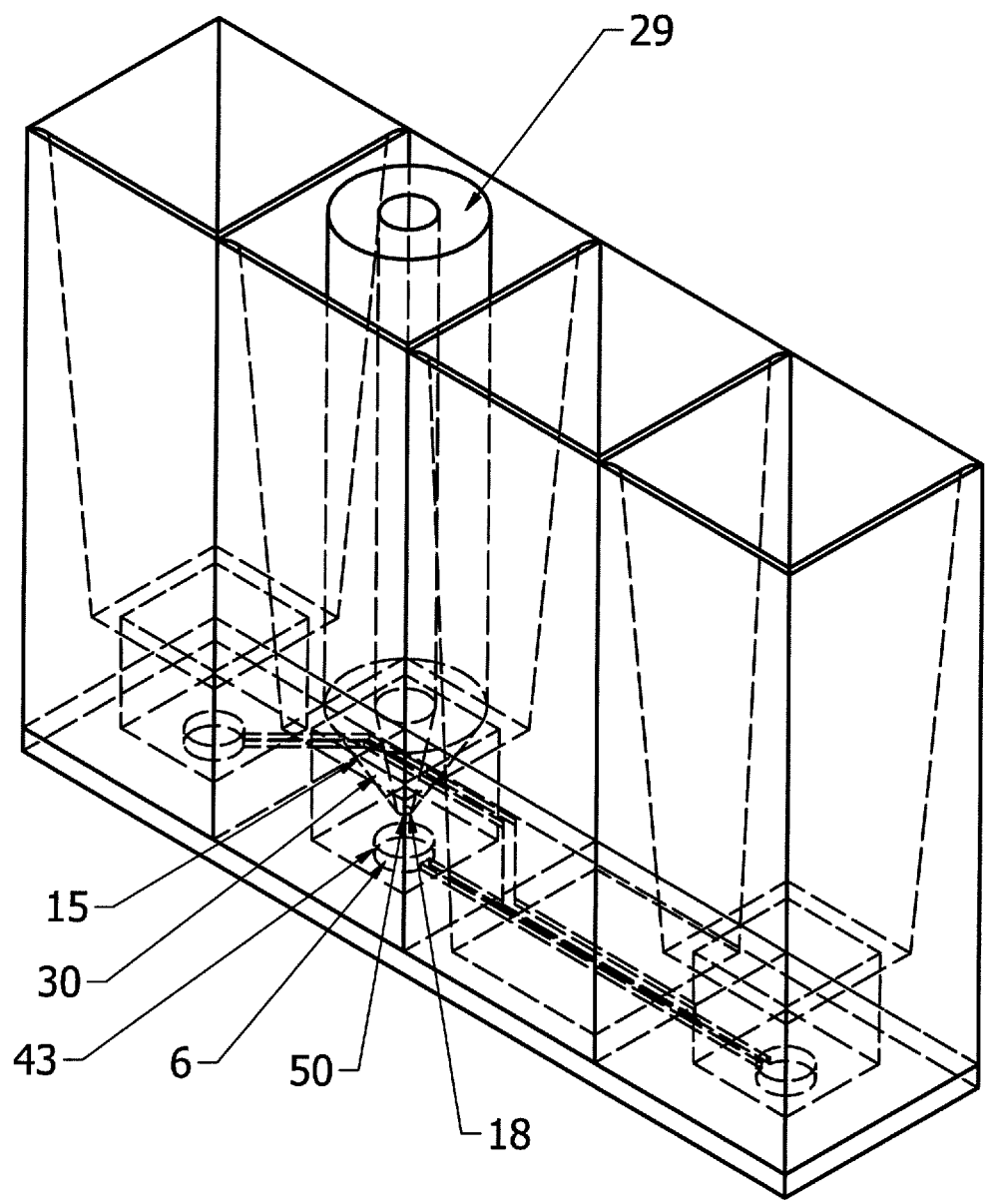

FIG. 5a shows the top view of the FIG. 4a, wherein a dispensing part 29 of a fluid dispenser 28 is received in the opening 9 of the support structure 8 and supported by the support members 10. FIG. 5a shows a first embodiment of the kit of parts 27 according to the invention. FIG. 5b shows a view in cross section along line VB-VB of FIG. 5a. FIG. 5c shows a view in cross section along line VC-VC of FIG. 5a. FIG. 5d shows a view in cross section along line VD-VD of FIG. 5b. FIG. 5e schematically shows a view in perspective of the first embodiment of the kit of parts 27 according to the invention of FIG. 5a.

The shown kit of parts 27 comprises a microfluidic plate 1 and a fluid dispenser 28, such as a pipette, having a dispensing part 29 from which in use a fluid is dispensed. The dispensing part 29 comprises an end 30 having the form of a right circular cone 15 or a truncated right circular cone 16.

The end 30 of the dispensing part 29 fits within the first empty space 14 of the support structure 8 and the end 30 of the dispensing part 29 is supported by the at least one support member 10 when received in the opening 9.

The end 30 of the dispensing part 29 has the form of a right circular cone 15 and an apex 18 thereof is located vertically above the inlet chamber 6 and at a distance from the bottom surface 7 when the end 30 is received in the opening 9 and supported by the at least one support member 10.

The apex 18 which is located vertically above the inlet chamber 6 will be in contact with a line extending through the inlet chamber 6 and perpendicular to the second plane 7. The vertical lines 42 shown in FIG. 5b extend through the outer edge 43 of the inlet chamber 6. The apex 18 being located vertically above the inlet chamber 6 will be located between said vertical lines 42.

The outer edge 43 of the inlet chamber 6 is also shown in the top view of FIG. 4a. The apex 18 being located vertically above the inlet chamber 6 will be located within said outer edge 43 when seen from said top view.

The second empty space 21 forms a vent 31 to allow fluid communication between the inlet chamber 6 and the surrounding environment 34 when the end 30 of the dispensing part 29 is received in the opening 9 and supported by the at least one support member 10.

Clearly also multiple vents 31 may be formed as part of the invention.

The openings 9 as defined by at least part of the support structures 8 of the microfluidic plate 1 are located at a predetermined distance from each other that is a multiple of the pitch between wells that are used in standard microtiter plates. This pitch is typically 2.25 mm, 4.5 mm, 9 mm coinciding with 1536, 384 and 96 well plates respectively. The fluid dispenser 28 may comprise multiple dispensing parts that are spaced according to a standard multipipette and robot head dispensers having dispensing ends that correspond with the pitch of the respective inlets.

The kit of parts 27 of FIG. 5 comprises a fluid dispenser 28, such as a pipette, having a dispensing part 29 with an end 30 from which in use a fluid is dispensed, and a microfluidic plate 1 comprising a plurality of microfluidic networks 2 and inlets 3 providing access to the microfluidic networks 2. Each microfluidic network 2 comprises a capillary pressure barrier 4. Each inlet 3 is formed by an inlet chamber 6 having a bottom surface 7. A support structure 8 is provided above each inlet 3. The support structure 8 defines an opening 9 to receive the end of the dispensing part 29. The support structure 8 comprises at least one support member 10 to support the end 30 of the dispensing part 29 in order to block movement of the dispensing part 29 received in the opening 9 towards the bottom surface 7 of the inlet 3 beyond a predetermined distance from the bottom surface 7. The support structure 8 is configured to position the end 30 of the dispensing part 29 received in the opening 9 and supported by the at least one support member 10 vertically above or in the inlet chamber 6. The support structure 8 comprises a vent 13 allowing fluid communication between the inlet chamber 6 and the surrounding environment 34 when the end 30 of the dispensing part 29 is received in the opening 9 and supported by the at least one support member 10.

The end 30 of the dispensing part 29 has a longitudinal axis 32, and a circular form in a cross section perpendicular to the longitudinal axis 32, and the opening 9 of the support structure 8 has a non-circular form in a plane 12 extending parallel to the microfluidic network 2.

At least part of the conically shaped end 30 of the dispensing part 29 has a diameter of D1 in the cross section perpendicular to the longitudinal axis 32. The at least one support member 10 is positioned at the opening 9 such that a circle 11 can be defined in the plane 12 extending parallel to the microfluidic network 2, which circle 11 has the largest possible diameter while being completely located within the opening 9 and in contact with the at least one support member 10. The circle 11 has a diameter D2 which is smaller than the diameter D1.

Movement of the dispensing part 29 received in the opening 9 and supported by the at least one support member 10 is blocked in any direction parallel to the microfluidic network 2, more specifically to the plane 12.

The end 30 of the dispensing part 29 has the form of a right circular cone 15 and the apex 18 thereof is located vertically above the inlet chamber 6 and at a distance from the bottom surface 7 when the end 30 is received in the opening 9, more specifically in the circle 11 defined by the at least one support member 10, and supported by the at least one support member 10. In an alternative embodiment, the apex 18 is located in the inlet chamber 6 and at a distance from the bottom surface 7 when the end is received in the opening 9, more specifically in the circle 11 defined by the at least one support member 10, and supported by the at least one support member 10. A discharge opening 50 (from which the fluid is discharged) is located at the apex 18 of the conically shaped end 30 of the discharge part 29.

The support structure 8 comprises four support members 10 and each support member 10 is configured to have one contact area with the end 30 of the dispensing part 29.

The method of filling the microfluidic network 2 of the microfluidic plate 1 of FIG. 1, comprising the steps of:
providing the kit of parts 27 of FIG. 5, and
placing the end 30 of the dispensing part 29 of the fluid dispenser 28 in the opening 9 of one of the support structures 8 of the microfluidic plate 1 such that the end 30 is supported by the at least one support member 10 to position the dispensing part 29 vertically above or in the respective inlet chamber 6, and
discharging a liquid or gel or gel precursor in the inlet chamber 6 via the dispensing part 29 received in the opening 9 and supported by the at least one support member 10.

Figure 6A:
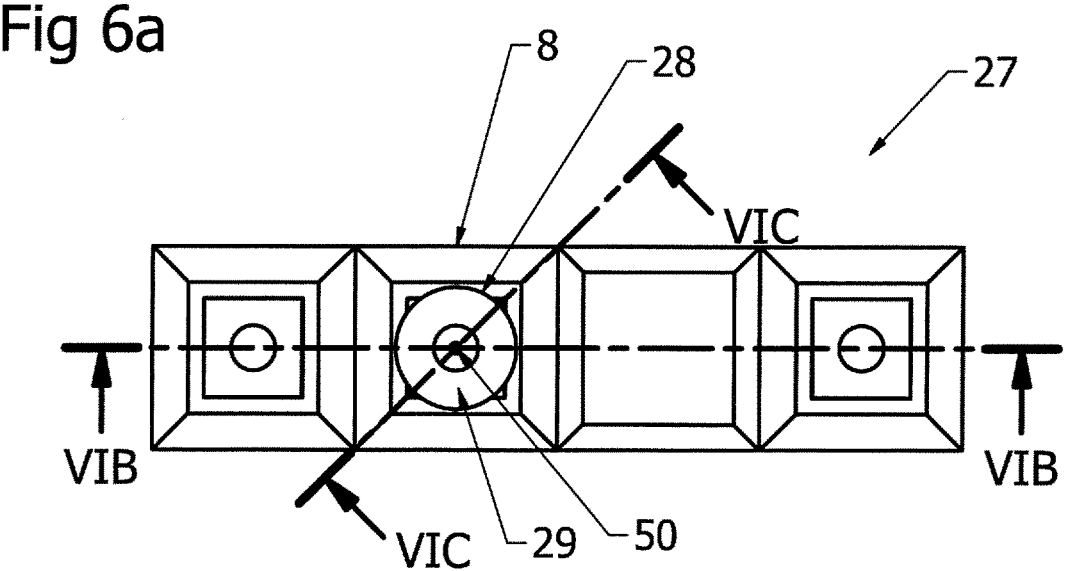
Figure 6B:
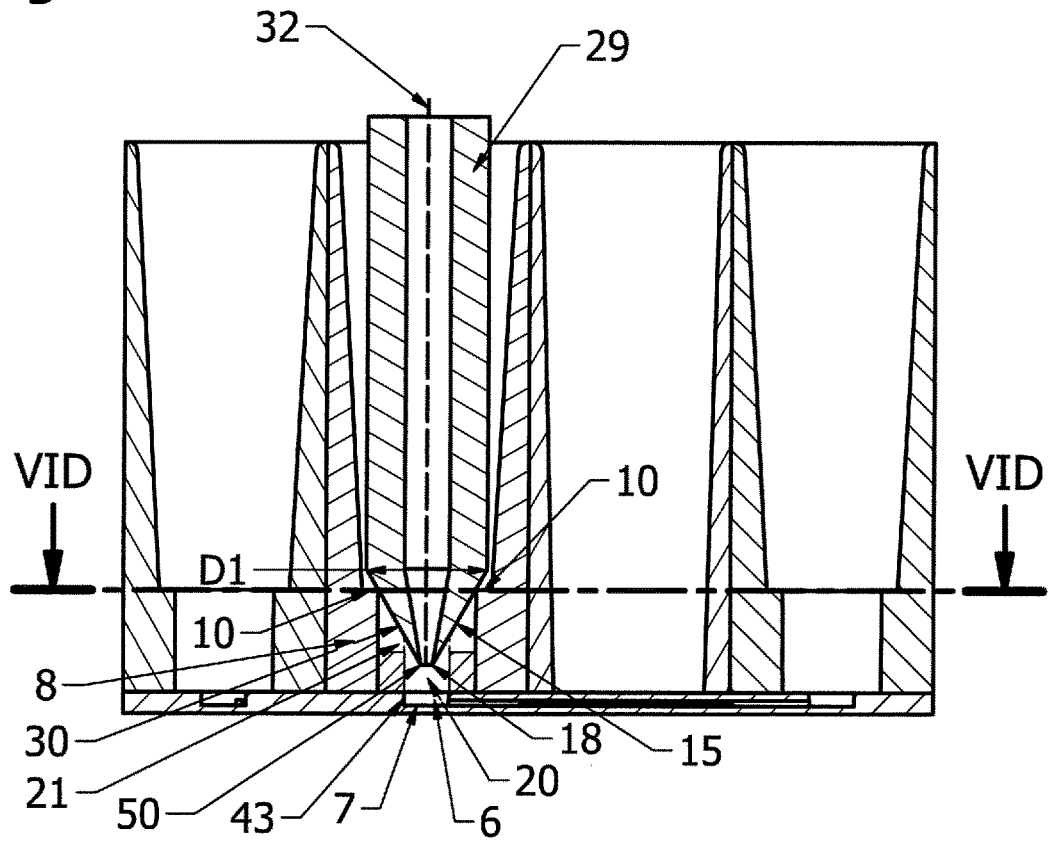
Figure 6C:
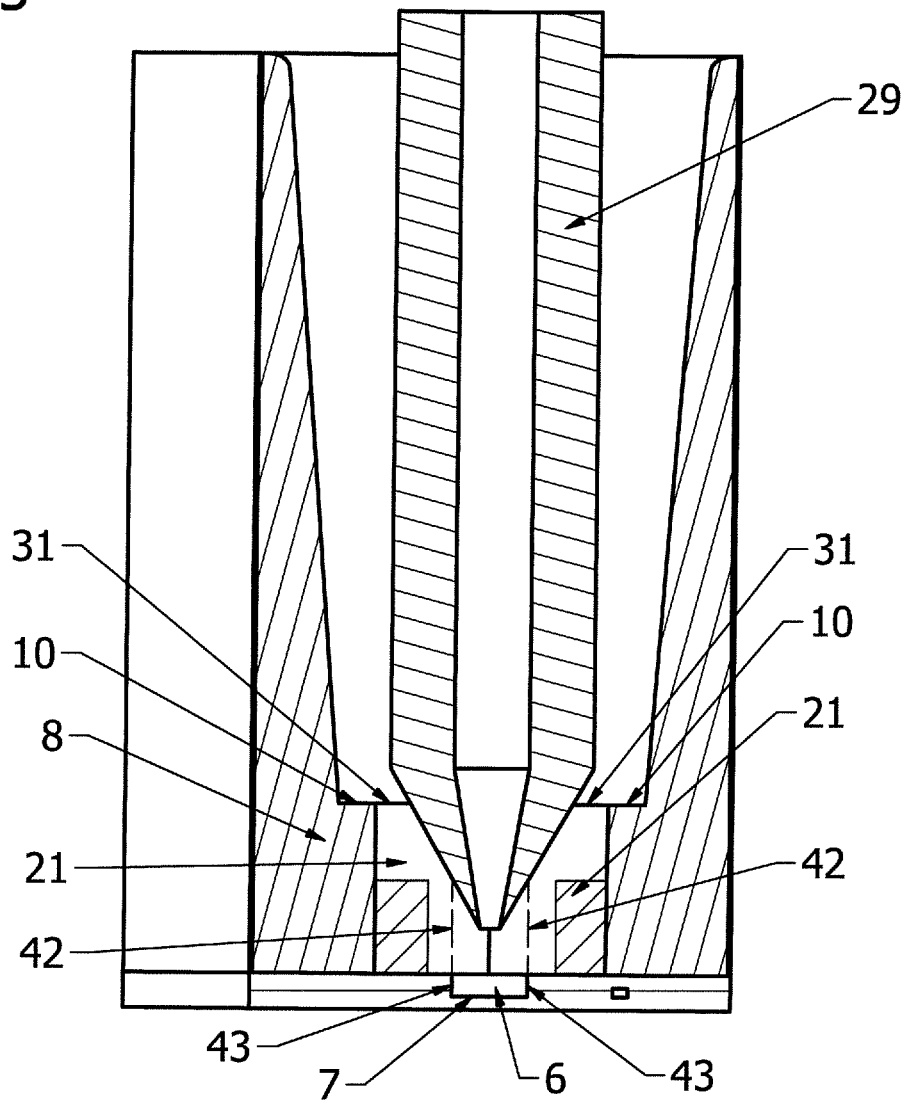
Figure 6D:
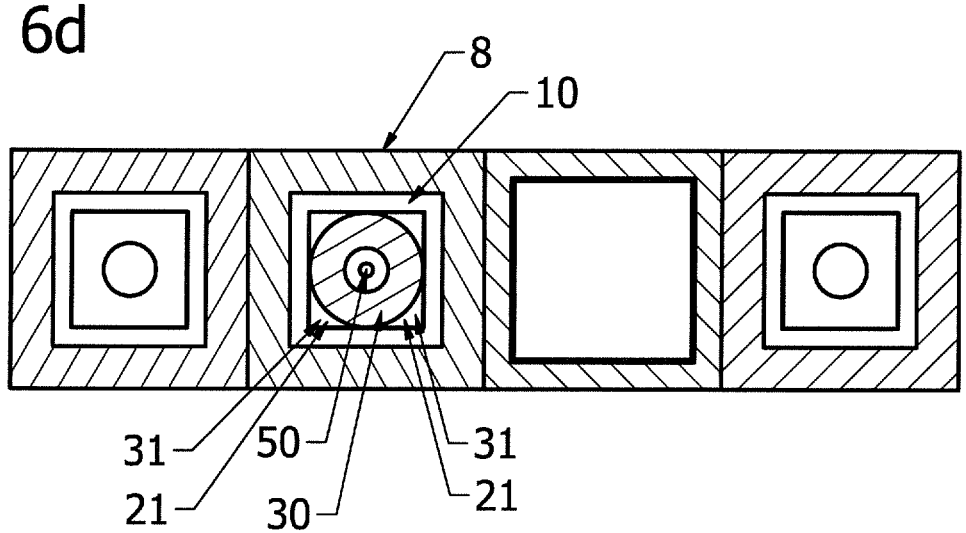

FIG. 6a shows a top view of a second embodiment of the kit of parts 27 according to the invention, wherein the end 30 of the dispensing part 29 has the form of a right circular cone 15. FIG. 6b shows a view in cross section along line VIB-VIB of FIG. 6a. FIG. 6c shows a view in cross section along line VIC-VIC of FIG. 6a. FIG. 6d shows a view in cross section along line VID-VID of FIG. 6b.

Figure 7A:
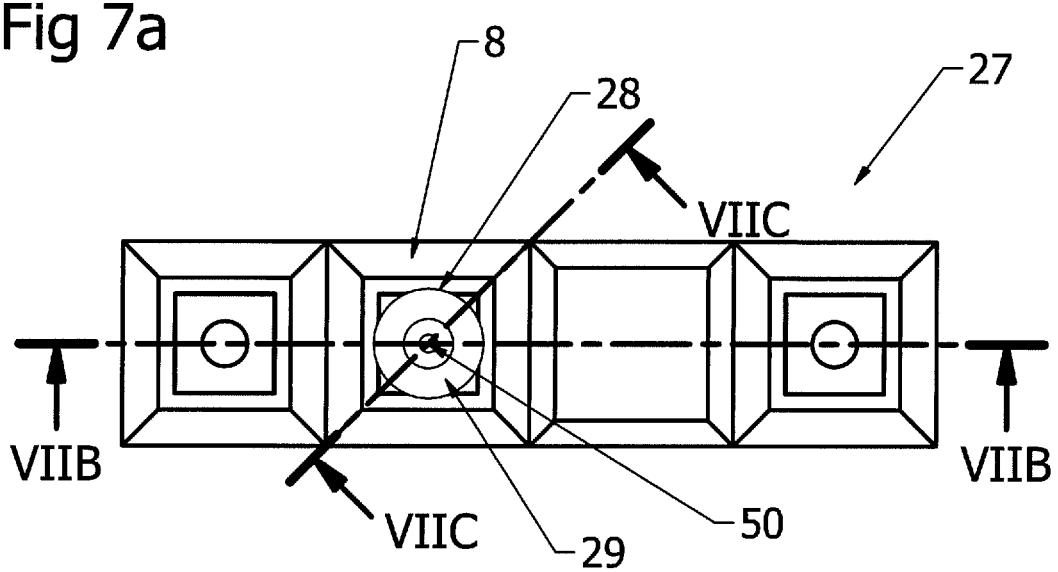
Figure 7B:
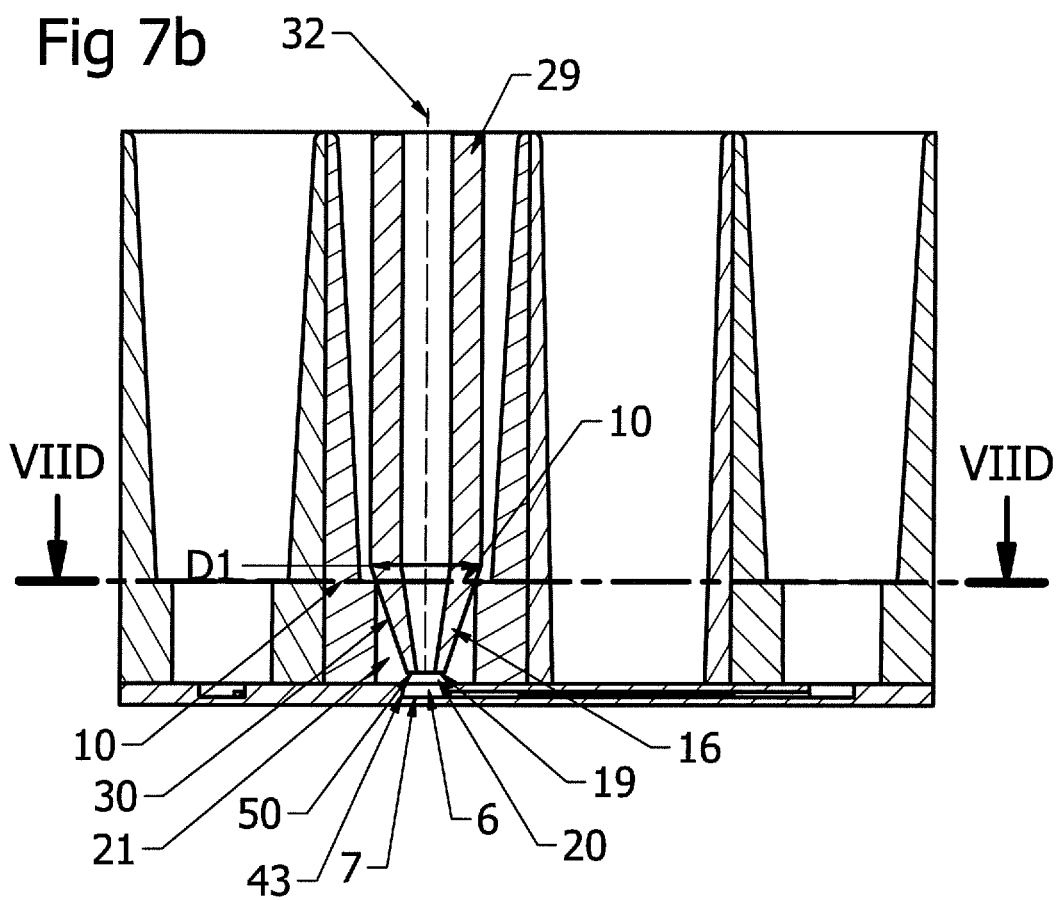
Figure 7C:
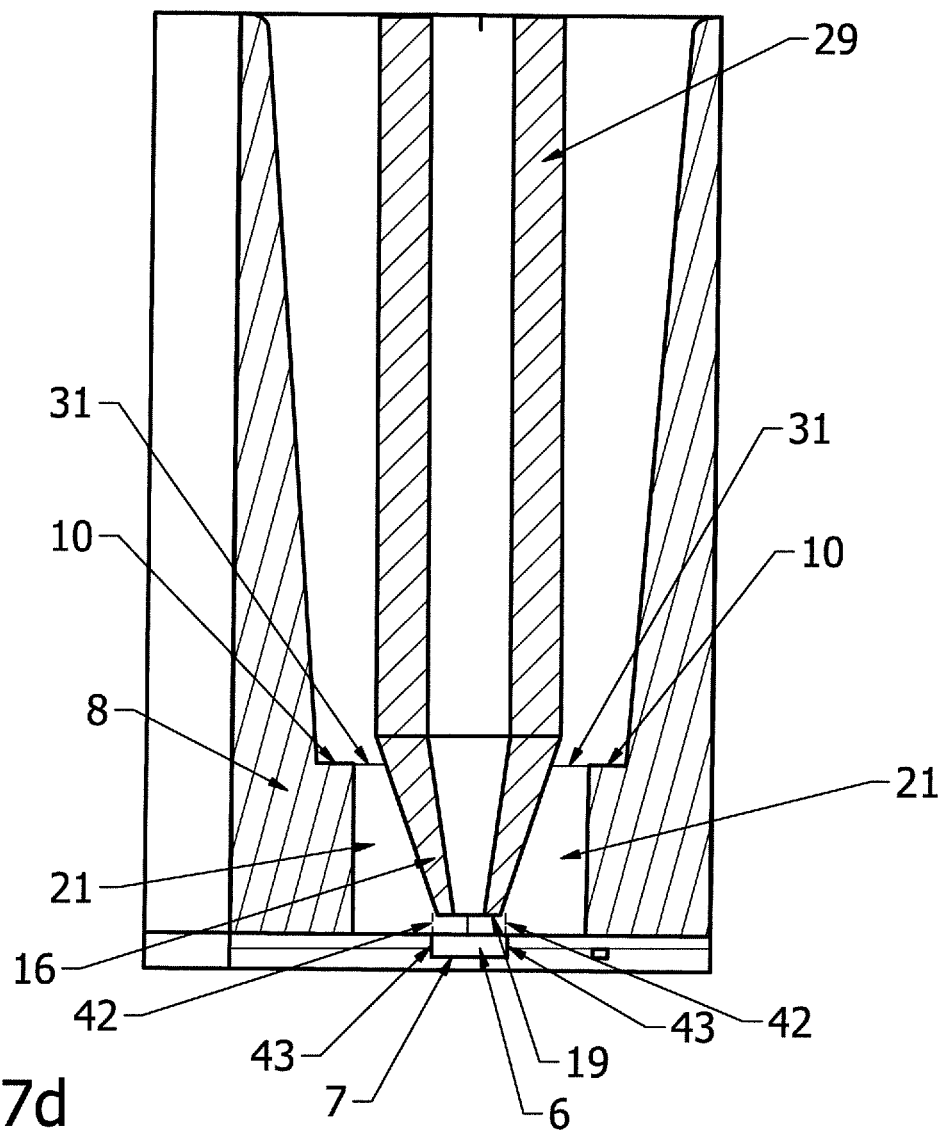
Figure 7D:
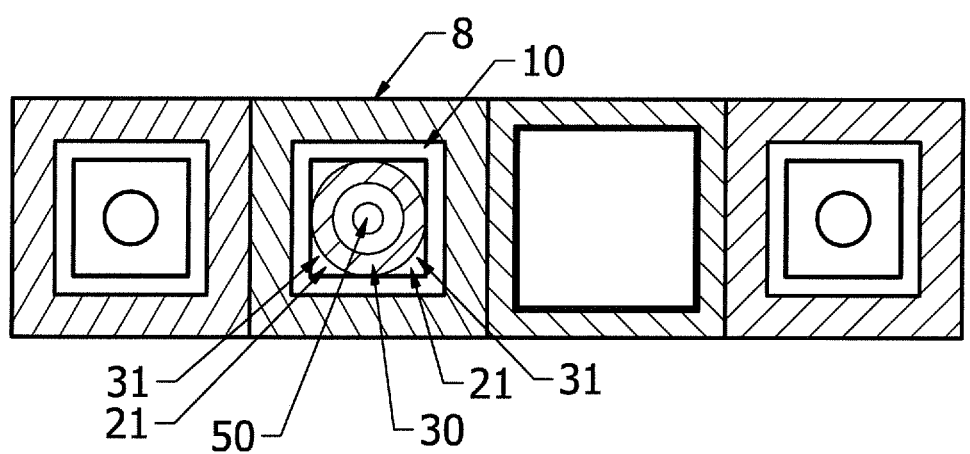

FIG. 7a shows a top view of a third embodiment of the kit of parts 27 according to the invention, wherein the end 30 of the dispensing part 29 has the form of a truncated right circular cone 16. FIG. 7b shows a view in cross section along line VIIB-VIIB of FIG. 7a. FIG. 7c shows a view in cross section along line VIIC-VIIC of FIG. 7a. FIG. 7d shows a view in cross section along line VIID-VIID of figure b.

The end 30 of the dispensing part 29 has the form of a truncated right circular cone 16 and the apical surface 19 is located vertically above the inlet chamber 6 and at a distance from the bottom surface 7 when the end 30 is received in the opening 9, more specifically in the circle 11 defined by the at least one support member 10, and supported by the at least one support member 10. In an alternative embodiment, the apical surface 19 is located in the inlet chamber 6 and at a distance from the bottom surface 7 when the end 30 is received in the opening 9, more specifically in the circle 11 defined by the at least one support member 10, and supported by the at least one support member 10. A discharge opening 50 (from which the fluid is discharged) is located at the apical surface 19, more specifically at the centre of the apical surface 19, of the end 30 of the discharge part 29.

Figure 8C:
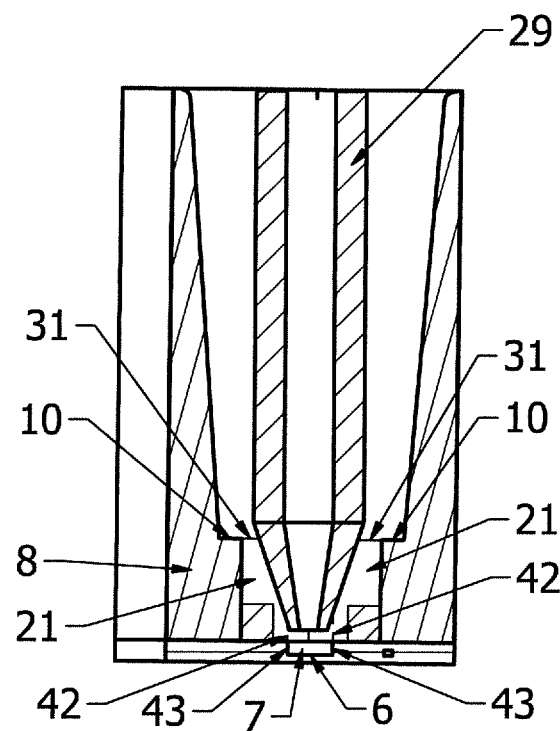
Figure 8D:
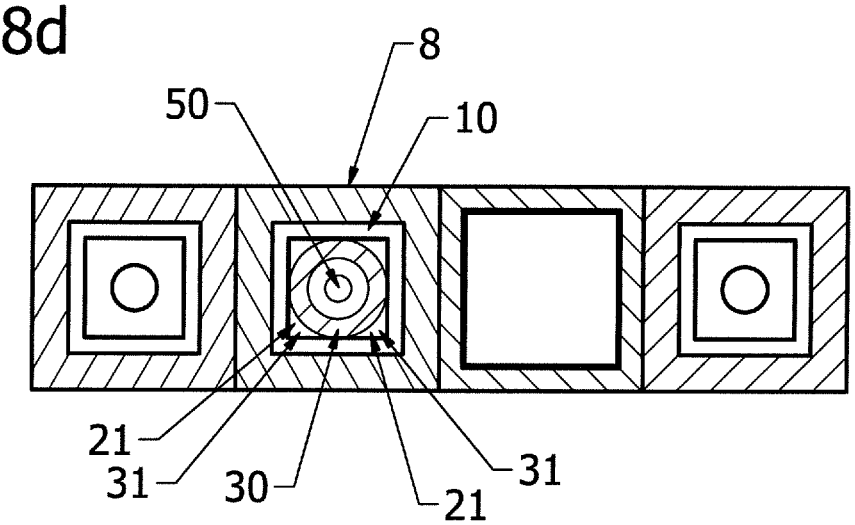

FIG. 8a shows a top view of a fourth embodiment of the kit of parts 27 according to the invention, wherein the end 30 of the dispensing part 29 has the form of a truncated right circular cone 16. FIG. 8b shows a view in cross section along line VIIIB-VIIIB of FIG. 8a. FIG. 8c shows a view in cross section along line VIIIC-VIIIC of FIG. 8a. FIG. 8d shows a view in cross section along line VIIID-VIIID of FIG. 8b.

Figure 9A:
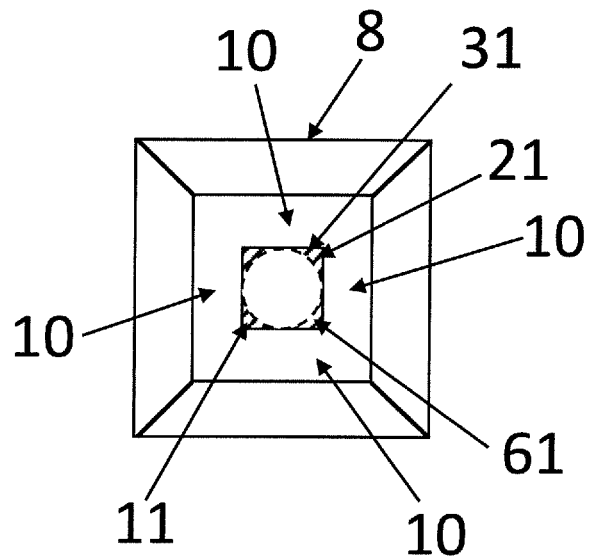

FIG. 9a shows a top view of a single support structure 8 of FIG. 1. The support structure 8 comprises four support members 10 and each support member 10 is configured to have one contact area with the end 30 of the dispensing part 29. The support structures 8 are connected to each other. The circle 11 defined by the support members 10 is indicated. A vent area 61 of the second plane 12 extends between the support structure 8, more specifically the support members 10, and the circle 11. The vent area 61 is larger than a channel area 62 formed by an in use vertical cross section perpendicular to the longitudinal axis of the microfluidic channel 35 as depicted by line XD in FIG. 10a (see FIG. 10d).

Figure 9B:
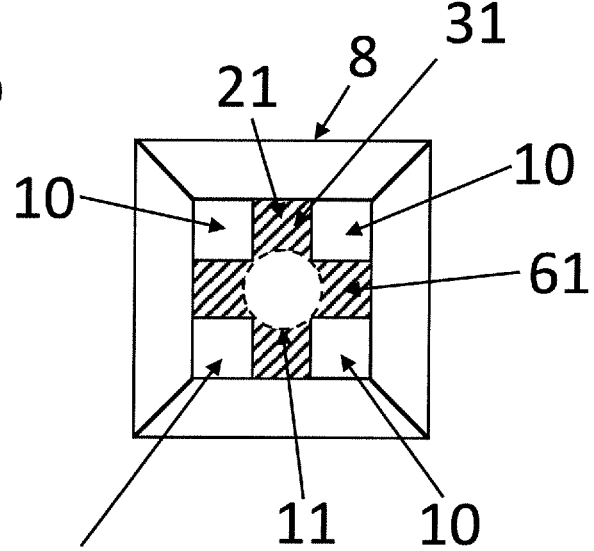

FIG. 9b shows a top view of an alternative embodiment of the support structure 8 of FIG. 9a. The support structure 8 comprises four support members 10 located at a distance from each other. Also the vent area 61 is shown.

Figure 9C:
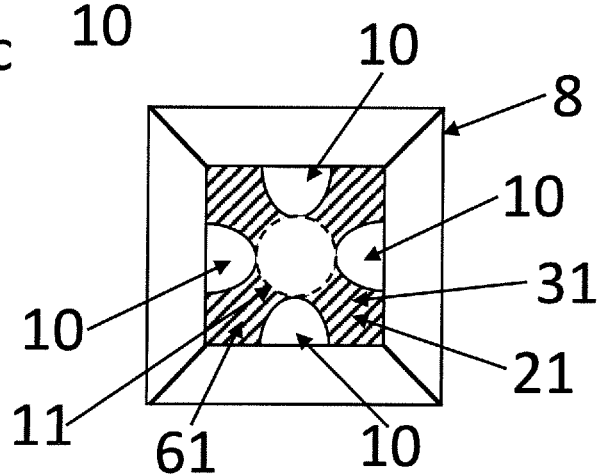

FIG. 9c shows a top view of another alternative embodiment of the support structure 8 of FIG. 9a. The support structure 8 comprises four support members 10 located at a distance from each other.

Figure 10C:
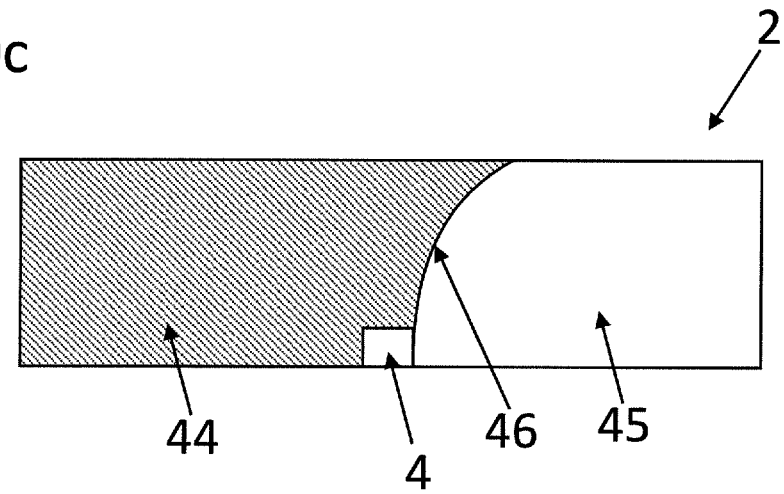

FIG. 10a shows a top view of a single microfluidic network of FIG. 1. The microfluidic network 2 comprises a first microfluidic channel 35 which is connected to the first inlet 3A and a second microfluidic channel 36 which is connected to the second inlet 3B and a third microfluidic channel 37 that is connected to the third inlet 3C. A capillary pressure barrier 4 is dividing the microfluidic chamber 38 into a first part 39 and a second part 40. The first microfluidic channel 35 is communicating with the first part 39 of the microfluidic chamber 38, while the second microfluidic channel 36 and the third microfluidic channel 37 are communicating with the second part 40 of the microfluidic chamber 38. FIG. 10b shows an enlarged view of the part XB of the microfluidic network 2 of FIG. 10a in horizontal cross section at the vertical level of the capillary pressure barrier. In some embodiments of the microfluidic plate 1 according to the invention, said part corresponds to what can be seen through the viewing window 33 of the microfluidic plate 1. A liquid 44 is located in the first half of the microfluidic channel and is pinned on the capillary pressure barrier 4. FIG. 10c shows a view in vertical cross section along line XC-XC of FIG. 10b, showing the liquid 44 being pinned on the capillary pressure barrier 4 and the air 45 present in the microfluidic network 2. The liquid-air meniscus 46 is clearly shown in FIG. 10c.

It should be remarked that the meniscus in FIG. 10c stretches beyond the capillary pressure barrier and has a concave shape. This is by example only. The meniscus may also have a convex shape, but would in almost all cases extend beyond the capillary pressure barrier.

Figure 10D:
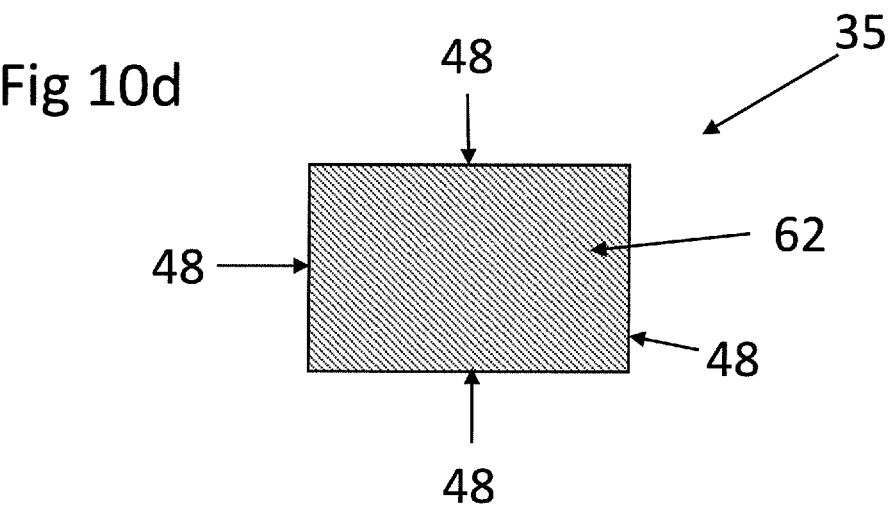

FIG. 10d shown a cross sectional view perpendicular to the first microfluidic channel 35. The channel area 62 through which the liquid can flow is clearly shown. The channel area 62 is defined by the channel walls 48 of the microfluidic channel 35. FIG. 10d shows an exemplary rectangular cross section of the channel 35. This need not necessarily be rectangular. On the contrary a typical cross section is trapezoidal of shape, as well as semi-circular. The cross sectional channel shape depends strongly on the manner of manufacturing of the microfluidic channel 35.

Figure 11A:
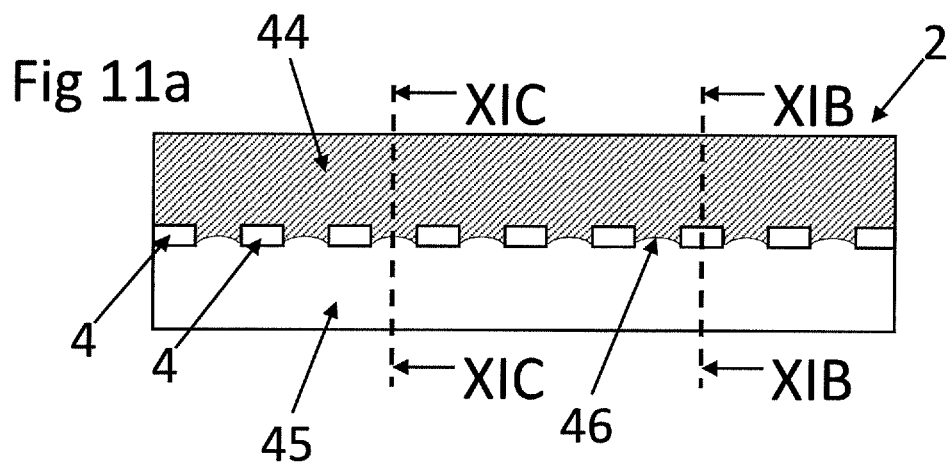
Figure 11B:
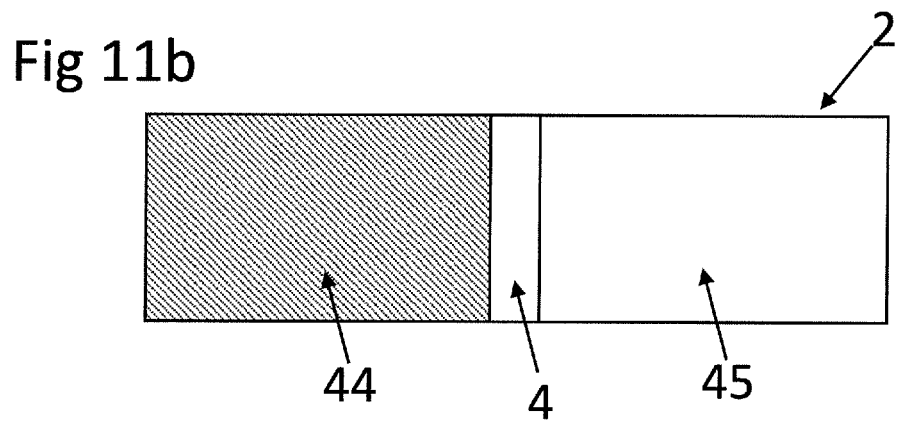
Figure 11C:
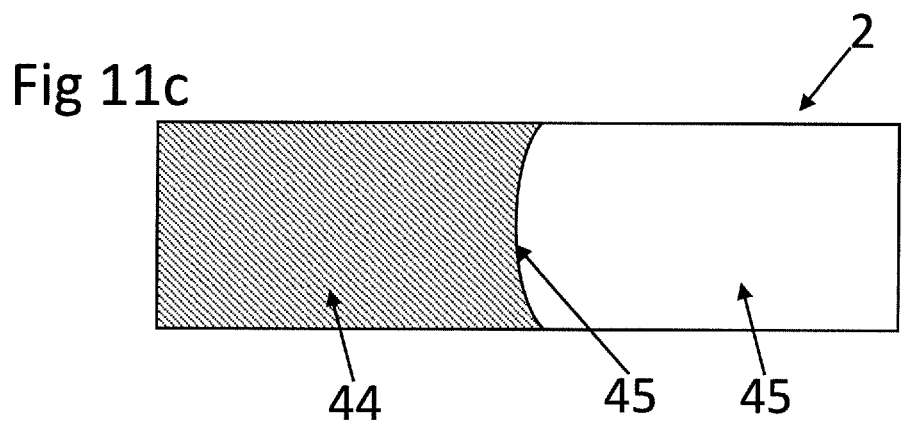
Figure 12A:
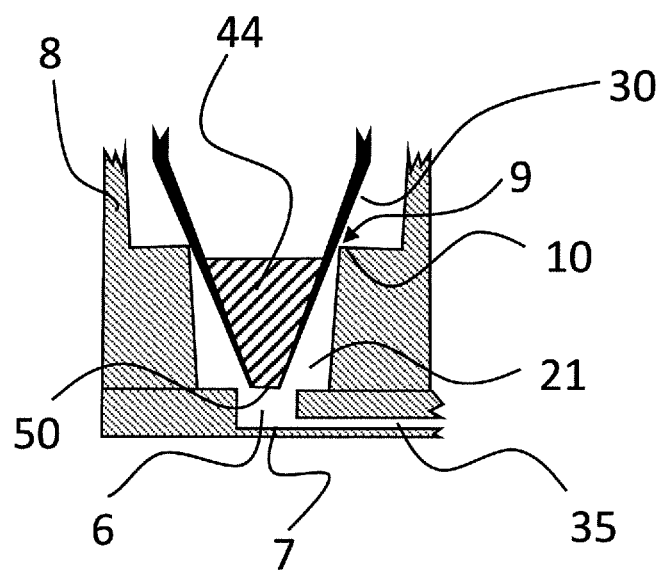
Figure 12B:
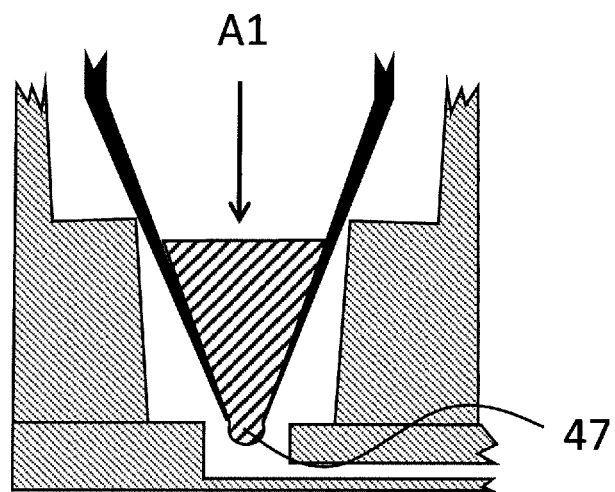
Figure 12C:
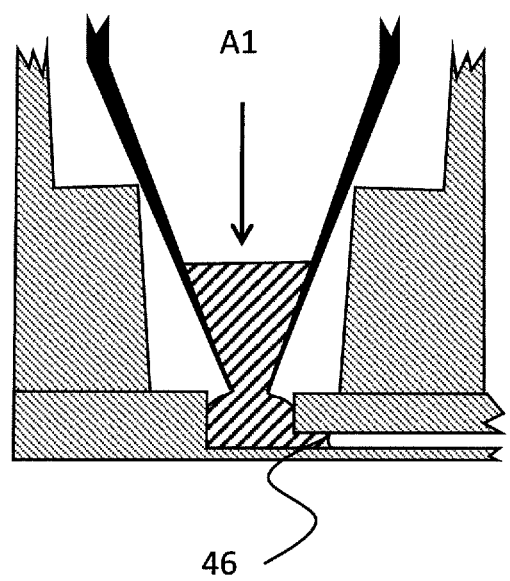
Figure 12D:
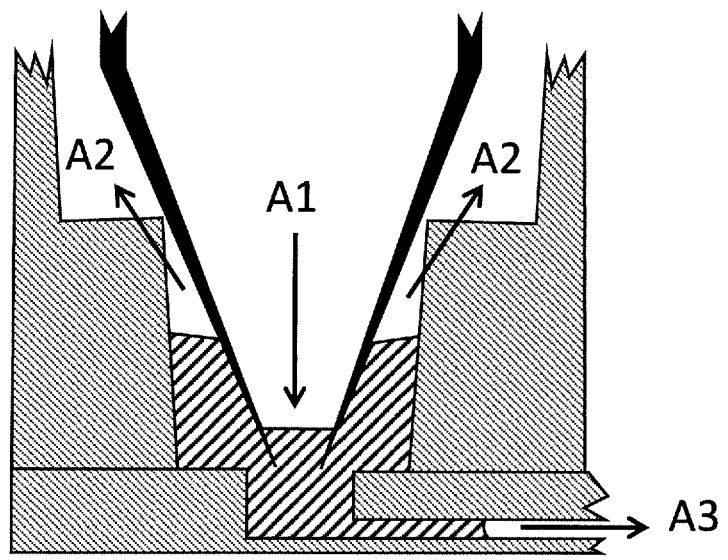
Figure 12E:
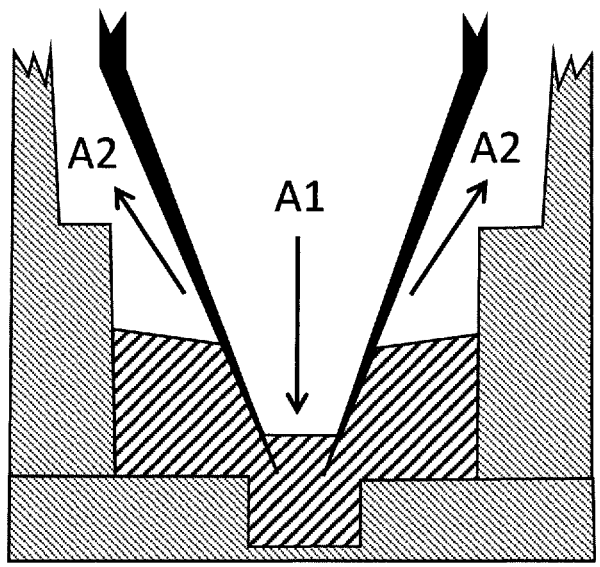

FIG. 11a view in horizontal cross section similar to FIG. 10b of an alternative embodiment of the capillary pressure barrier 4. FIG. 11b shows a view in vertical cross section along line XB-XB of FIG. 11a. FIG. 11c shows a view in vertical cross section along line XC-XC of FIG. 11a. The liquid-air meniscus 44 is pinned by the capillary pressure barrier 4.

FIG. 12 shows the operation of the microfluidic plate and kit of parts according to the invention. FIG. 12a depicts in vertical cross section along a line similar as the line VB of FIG. 5a. A dispensing part 29 with conical apex that is supported by at least two support members 10. The dispensing part is located vertically above the inlet chamber 6 and is loaded with a fluid 44. FIG. 12b-d depict various phases of discharging of the contents of the dispensing means in the same cross sectional view as FIG. 12a. FIG. 12e shows the same phase as FIG. 12d, but in a vertical cross section along a line similar as the line VC of FIG. 5a. In a first step a droplet 47 is formed that is suspended from the discharging opening 50 by capillary forces. The arrow A1 symbolizes the efflux of fluid from the dispensing part. Upon further ejection of the fluid, the droplet touches the bottom surface 7 of the microfluidic network and/or the sidewalls of the inlet chamber 6. A liquid-air meniscus 46 enters the microfluidic channel 35. Upon further ejection of fluid from the dispensing part, part of the inlet chamber and possibly part of the second empty space are filled up with liquid. Build-up of pressure is prevented by efflux of air from the inlet chamber and second empty space as depicted by the arrows A2. The liquid-air meniscus 46 progresses into the microfluidic channel by capillary forces primarily as depicted by the arrow A3. It is obvious to a person skilled in the art that this process is not limited to this specific order of events in filling. It is for example possible that the dispensed droplet will be fully ejected and detached from the dispensing part before touching the bottom surface. Additionally, after the complete droplet is dispensed, air can be ejected requiring further venting.

The fluid ejection flux from the dispensing part is almost fully decoupled from meniscus progression in the microfluidic network, since the hydraulic resistance of the free part of the opening 9 (the vent area 61 in the second plane 12 extending between the dispensing part and the support structure) is much lower than the hydraulic resistance of the microfluidic channel. The pipette pressure with which a fluid is expelled is thus almost fully decoupled from meniscus progression. In addition to capillary forces to advance the liquid meniscus, gravity of the fluid column on top of the inlet may play a role. Also the pressure drop over the meniscus in the inlet chamber or second empty space may influence liquid-air meniscus progression in the microfluidic channel.

An example of method of use of the microfluidic plate and kit according to the invention is the so-called 3D cell culture and boundary culture. For this purpose a gel precursor (typically from an extracellular matrix (ECM) gel, such as collagen, fibrinogen, fibronectin, basement membrane extract such as Matrigel or synthetic gels) is introduced into an inlet of the microfluidic plate with a pipette (typically a repeating pipette such as the Eppendorf Multipette® M4 (Eppendorf AG, Germany, catalogue number 4982 000.012) in combination with Eppendorf Combitips Advanced® (Eppendorf AG, Germany, catalogue number 0030 089.405). The gel precursor further contains cells yielding a cell suspension. The pipette tip is supported on one or more support members and the ECM gel precursor is released into the inlet of the microfluidic plate. The gel precursor is transported into the microfluidic network by capillary forces, potentially assisted by gravity. The gel is subsequently halted by a phaseguide similar to 4 in FIG. 10A, which is essentially a capillary pressure barrier that spans the complete width of a microfluidic chamber. The gel precursor is caused to gelate, prior to introduction of a second fluid. This second fluid is typically a growth medium that provides nutrients and oxygen. In the case of a flow, the growth medium may also remove or dilute waste metabolites as produced by the cells.

In the above example it is of critical importance that the phaseguide or capillary pressure barrier is not breached when loading the gel precursor. Breaching the phaseguide would lead to the gel filling at least part of the ulterior network, possibly partially blocking fluid flow through the ulterior network and/or hampering the subsequent filling with growth medium. Thus the functioning of the device is incorrect.

In a similar manner as the above example, cells can be introduced in the second fluid, thereby depositing them against the gel. Upon bringing these cells in culture, they typically form a tube that can be perfused with a flow through the lumen of the tube. A malfunctioning device that suffers from unintended breaching of the capillary pressure barrier would not enable such tube growth in the microfluidic network in a correct manner.

In yet another example, multiple gels could be patterned adjacent to one another. Multiple gels can be patterned by injecting gel precursors, halting advancement of the precursors by a capillary pressure barrier and causing the precursors to gellate in different parts of the netword sequentially. Suspension of a first cell type in a first gel precursor, followed by a second cell type in a second gel precursor results in a so-called stratified co-culture, in which cell types cultured adjacent to one another. Clearly the microfluidic structure of FIG. 10A is not sufficient to accommodate multiple gels and a perfusion flow, but would require additional inlets, channels and capillary pressure barriers to accommodate the additional gels.

In another example of use of the microfluidic plate and kit of parts according to the invention, an assay could be performed in which a first fluid containing analytes or reagents are selectively patterned in the microfluidic network, followed by addition of a second fluid containing a second reagent or analyte. The method further relates to causing the two reagents and/or analyte to interact, yielding a signal that relates to the analyte under investigation. An example could be an immunoassay including a target molecule as analyte including a detection antibody that can bind to the target molecule and may contain a fluorescent label. Alternatively an immobilized capture antibody can capture the analyte, followed by a second reagent that binds to the analyte and a third reagent that may contain a fluorescent label that detects the second reagent bound to the analyte. Other examples of use include ELISAs, PCR assays, protein crystalisation assays, microarray experiments, and next generation sequencing assays.

Example Construction

The microfluidic plate according to the invention may be constructed in a variety of manners. In a first embodiment, the support structure and the guiding structure are made out of polymer such as polystyrene, cyclo olefin plymer or copolymer (COP, COC), polymethyl methacrylate (PMMA) or polycarbonate. The microfluidic network is constructed separately and comprises polymer or glass top and bottom substrates. The microfluidic network may be constructed wither by etching the network into either substrate or by patterned in a polymer layer on top of either substrate. In a particular versatile embodiment of the invention, at least one of the top or bottom substrate is constructed out of glass or a hydrophilic polymer, such that fluid transport may be achieved by capillary forces only. In this same particularly versatile embodiment according to the invention, the capillary pressure barrier is constructed out of a polymeric material that is less hydrophilic than the glass or hydrophilic polymer.

In this same embodiment, the support and guiding structures are part of a microtiter plate user interface that could be injection moulded. The microfluidic plate could be constructed using photolithography techniques, hot-embossing techniques, soft embossing techniques, etching techniques, replication moulding or injection moulding techniques.

In yet another embodiment, the microtiter plate user interface contains elements of the microfluidic network that is injection moulded in one piece. The microfluidic network needs to be subsequently sealed or bonded to a bottom substrate.

The invention further relates to a kit of parts, a method, and a microfluidic plate according to any of the following clauses.

1. Kit of parts (27) comprising:
    a fluid dispenser (28), such as a pipette, having a dispensing part (29) with an end (30) from which in use a fluid is dispensed, and
    a microfluidic plate (1) comprising a plurality of microfluidic networks (2) and inlets (3) providing access to the microfluidic networks, wherein;
        each microfluidic network comprises a capillary pressure barrier (4),
        each inlet is formed by an inlet chamber (6) having a bottom surface (7),
        a support structure (8) is provided above each inlet, which support structure defines an opening (9) to receive the end of the dispensing part and comprises at least one support member (10) to support the end in order to block movement of the dispensing part received in the opening towards the bottom surface of the inlet beyond a predetermined distance from the bottom surface,
        the support structure is configured to position the end of the dispensing part received in the opening and supported by the at least one support member vertically above or in the inlet chamber, and
        the support structure comprises a vent (31) allowing fluid communication between the inlet chamber and the surrounding environment (34) when the end of the dispensing part is received in the opening and supported by the at least one support member.
2. Kit of parts according to clause 1, wherein
    the end of the dispensing part has a longitudinal axis, and a circular form in a cross section perpendicular to the longitudinal axis, and
    the opening of the support structure has a non-circular form in a plane extending parallel to the microfluidic network.
3. Kit of parts according to clause 2, wherein
    at least part of the end of the dispensing part has a diameter of D1 in the cross section perpendicular to the longitudinal axis,
    the at least one support member is positioned at the opening such that a circle can be defined in the plane extending parallel to the microfluidic network, which circle has the largest possible diameter while being completely located within the opening and in contact with the at least one support member, and
    the circle has a diameter D2 which is smaller than the diameter D1 of the end of the dispensing part.
4. Kit of parts according to any of the preceding clauses, wherein movement of the dispensing part received in the opening and supported by the at least one support member is blocked in any direction parallel to the microfluidic network.
5. Kit of parts according to any of the preceding clauses, wherein a guiding structure to guide the dispensing part towards the opening is provided on top of the support structure.
6. Kit of parts according to clause 5, wherein the at least one support member is located between the inlet chamber and the guiding structure.
7. Kit of parts according to any of the preceding clauses, wherein the support structure is configured to form a reservoir to hold fluid, which reservoir is located above the inlet chamber.
8. Kit of parts according to clause 8, wherein the reservoir extends from the inlet chamber until the second plane.
9. Kit of parts according to clause 7 or 8, wherein the guiding structure is configured to form an additional reservoir to hold fluid, which additional reservoir is an extension of the reservoir.
10. Kit of parts according to any of the preceding clauses, wherein the support structures of the microfluidic plate are interconnected to form an integral structure.
11. Kit of parts according to any of the preceding clauses, wherein the microfluidic plate coincides with SBS microtiter plate dimensions.
12. Kit of parts according to any of the preceding clauses, wherein the end of the dispensing part has the form of a right circular cone or a truncated right circular cone.
13. Kit of parts according to any of the preceding clauses, wherein
    the end of the dispensing part has the form of a right circular cone and an apex thereof is located vertically above or in the inlet chamber and at a distance from the bottom surface when the end is received in the opening and supported by the at least one support member, or
    the end of the dispensing part has the form of a truncated right circular cone and the apical surface is located vertically above or in the inlet chamber and at a distance from the bottom surface when the end is received in the opening and supported by the at least one support member.
14. Kit of parts according to any of the preceding clauses, wherein the openings of at least part of the support structures of the microfluidic plate are located at a predetermined distance from each other and the fluid dispenser comprises multiple dispensing parts having ends located at a corresponding predetermined distance from each other.
15. Method of filling a microfluidic network, comprising the steps of:
    providing a kit of parts according to any of the clauses 1-14, and
    placing the end of the dispensing part of the fluid dispenser in the opening of one of the support structures of the microfluidic plate such that the end is supported by the at least one support member to position the dispensing part vertically above or in the respective inlet chamber, and
    discharging a liquid or gel or gel precursor in the inlet chamber via the dispensing part received in the opening and supported by the at least one support member.
16. Method according to clause 15, wherein
    the provided kit of part comprises the features of clause 14,
    the end of the discharge parts are placed in the openings of said at least part of the support structures such that the dispensing parts supported by the at least one support member to position the dispensing parts vertically above or in the respective inlet chambers, and
    a liquid or gel or gel precursor is discharged in the inlet chambers via the dispensing parts received in the openings and supported by the at least one support member.
17. Microfluidic plate comprising a plurality of microfluidic networks and inlets providing access to the microfluidic networks, wherein;

each microfluidic network comprises a capillary pressure barrier, each inlet is formed by an inlet chamber having a bottom surface, a support structure is provided above each inlet, which support structure defines an opening to in use receive a dispensing part of a fluid dispenser, such as a pipette, and comprises at least one support member to in use support an end of the dispensing part in order to block movement of the dispensing part received in the opening towards the bottom surface of the inlet beyond a predetermined distance from the bottom surface, the support structure is configured to in use position the end of the dispensing part received in the opening and supported by the at least one support member vertically above or in the inlet chamber, and the support structure comprises a vent allowing fluid communication between the inlet chamber and the surrounding environment when in use the end of the dispensing part is received in the opening and supported by the at least one support member.

18. Microfluidic plate that comprises a plurality of microfluidic networks and inlets providing access to the microfluidic networks, wherein;

each microfluidic network comprises a capillary pressure barrier and extends along a first plane, each inlet is formed by an inlet chamber having a bottom surface, a well is provided that is positioned above each inlet; each well having an inner volume as defined by the inner face of the walls of the well, the well further comprising at least one protrusion into the inner volume, the protrusion being the support member the at least one protrusion defines an opening such that a circle can be defined in a second plane extending parallel to the first plane, which circle has the largest possible diameter while being completely located within the inner volume and in contact with the at least one protrusion, and a first empty space is formed, which first empty space extends from the second plane towards the inlet chamber and has the form of a right circular cone or a truncated right circle cone, wherein the circle forms a base plane of the right circular cone or the truncated right circle cone, the microfluidic plate comprises the following features A or B;

A) an apex of the right circular cone or an apical surface of the truncated right circle cone is located in the inlet chamber and on the bottom surface, or B) an apex of the right circular cone or an apical surface of the truncated right circle cone is located vertically above or in the inlet chamber and at a distance from the bottom surface, wherein an additional empty space is formed extending from the apex or the apical surface until the bottom surface, and a second empty space is formed, which second empty space extends from the second plane into the inlet chamber and is located outside the first empty space.

As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Further, the terms and phrases used herein are not intended to be limiting, but rather, to provide an understandable description of the invention.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language, not excluding other elements or steps). Any reference signs in the claims should not be construed as limiting the scope of the claims or the invention.

It will be apparent to those skilled in the art that various modifications can be made to the microfluidic plate, the kit of parts and method without departing from the scope as defined in the claims.

The invention claimed is:

1. A microfluidic plate comprising:

a plurality of microfluidic networks, wherein each microfluidic network comprises a capillary pressure barrier and extends through a first plane;

inlets providing access to the plurality of microfluidic networks, wherein each inlet is formed by an inlet chamber having a bottom surface;

a support structure above each inlet, the support structure defining an opening and comprising at least one support member positioned at the opening such that a circle defined in a second plane extends parallel to the first plane, wherein the circle has the largest possible diameter while being completely located within the opening and in contact with the at least one support member, wherein the opening has a non-circular form at the second plane, wherein the support structure is configured such that a first empty space is formed, the first empty space extending from the second plane towards the inlet chamber, the first empty space having the form of a right circular cone or a truncated right circle cone, wherein the circle forms a base plane of the right circular cone or the truncated right circle cone;

and a second empty space is formed that extends from the second plane into the inlet chamber and is located outside the first empty space, wherein the second empty space forms a vent configured to allow fluid communication between the inlet chamber and the surrounding environment, wherein the microfluidic plate further comprises either:

A) an apex of the right circular cone or an apical surface of the truncated right circle cone that is located in the inlet chamber and on the bottom surface, or B) an apex of the right circular cone or an apical surface of the truncated right circle cone that is located vertically above or in the inlet chamber and at a distance from the bottom surface, wherein an additional empty space is formed extending from the apex or the apical surface until the bottom surface.

2. The microfluidic plate according to claim 1, wherein the inlet provides access to a microfluidic channel of the microfluidic network and a vent area of the second plane extending between the support structure and the circle that is larger than a channel area formed by a cross section perpendicular to the microfluidic channel.

3. The microfluidic plate according to claim 1, wherein the support structure comprises inner walls which surround the opening and the at least one support member extends in a transverse direction from the inner walls.

4. The microfluidic plate according to claim 1, wherein a guiding structure to in use guide an end of a dispensing part of a fluid dispenser towards the opening is provided on top of the support structure.

5. The microfluidic plate according to claim 3, wherein the at least one support member is located between the inlet chamber and the guiding structure.

6. The microfluidic plate according to claim 1, wherein the support structure is configured to form a reservoir to hold fluid, which reservoir is located above the inlet chamber.

7. The microfluidic plate according to claim 5, wherein the reservoir extends from the inlet chamber until the second plane.

8. The microfluidic plate according to claim 5, wherein the guiding structure is configured to form an additional reservoir to hold fluid, which additional reservoir is an extension of the reservoir.

9. The microfluidic plate according to claim 1, wherein the support structures of the microfluidic plate are interconnected to form an integral structure.

10. The microfluidic plate according to claim 1, wherein the microfluidic plate coincides with SBS microtiter plate dimensions.

11. The microfluidic plate according to claim 1, wherein the capillary pressure barrier is any one of:
   a hydrophobic patch, or stripe,
   a less hydrophilic patch or stripe with respect to the ulterior network material,
   a channel widening,
   one or more pillars or posts lined in a channel or chamber,
   a groove in the channel or chamber substrate, or
   a protrusion of the material into the chamber volume.

12. The microfluidic plate according to claim 1, wherein the inlets provide access to a microfluidic channel of the microfluidic network and the capillary pressure barrier is present in the microfluidic channel or a microfluidic chamber connected to the microfluidic channel.

13. A kit of parts comprising:
   the microfluidic plate according to claim 1;
   a fluid dispenser having a dispensing part from which in use a fluid is dispensed, wherein the dispensing part comprises an end having the form of a right circular cone or a truncated right circular cone.

14. The kit of parts according to claim 13, wherein the end of the dispensing part fits within the first empty space of the support structure and the end of the dispensing part is supported by the at least one support member when received in the opening.

15. The kit of parts according to claim 13, wherein the end of the dispensing part has the form of a right circular cone and an apex thereof is located in or vertically above the inlet chamber and at a distance from the bottom surface when the end is received in the opening and supported by the at least one support member, or the end of the dispensing part has the form of a truncated right circular cone and the apical surface is located in or vertically above the inlet chamber and at a distance from the bottom surface when the end is received in the opening and supported by the at least one support member.

16. The kit of parts according to claim 13, wherein the second empty space forms a vent to allow fluid communication between the inlet chamber and the surrounding environment when the end of the dispensing part is received in the opening and supported by the at least one support member.

17. A method of filling a microfluidic network, comprising the steps of:
   placing the end of the dispensing part of the fluid dispenser of the kit according to claim 13, in the opening of one of the support structures of the microfluidic plate such that the end is supported by the at least one support member to position the dispensing part vertically above or on the respective inlet chamber; and
   discharging a liquid or gel or gel precursor in the inlet chamber via the dispensing part received in the opening and supported by the at least one support.

18. The method according to claim 17, further comprising the step of venting the inlet chamber and/or the second empty space through a vent area in the second plane extending between the support structure and the end of the dispensing part.

19. The kit according to claim 13, wherein the fluid dispenser is a pipette.

* * * * *